US012403154B2

(12) United States Patent
Lightcap et al.

(10) Patent No.: US 12,403,154 B2
(45) Date of Patent: Sep. 2, 2025

(54) ADMINISTRATION OF STING AGONIST AND CHECKPOINT INHIBITORS

(71) Applicant: Takeda Pharmaceutical Company Limited, Osaka (JP)

(72) Inventors: Eric Scott Lightcap, Somerville, MA (US); Yosuke Sato, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 860 days.

(21) Appl. No.: 17/625,422

(22) PCT Filed: Jul. 9, 2020

(86) PCT No.: PCT/IB2020/056440
§ 371 (c)(1),
(2) Date: Jan. 7, 2022

(87) PCT Pub. No.: WO2021/005541
PCT Pub. Date: Jan. 14, 2021

(65) Prior Publication Data
US 2022/0257630 A1     Aug. 18, 2022

Related U.S. Application Data

(60) Provisional application No. 62/994,911, filed on Mar. 26, 2020, provisional application No. 62/944,650, (Continued)

(51) Int. Cl.
*A61K 31/7084* (2006.01)
*A61K 35/00* (2006.01)
*A61K 45/06* (2006.01)

(52) U.S. Cl.
CPC ......... *A61K 31/7084* (2013.01); *A61K 35/00* (2013.01); *A61K 45/06* (2013.01)

(58) Field of Classification Search
CPC .... A61K 31/7084; A61K 35/00; A61K 45/06; A61K 2039/545; A61K 2039/507;
(Continued)

(56) References Cited

U.S. PATENT DOCUMENTS

| 8,217,149 B2 | 7/2012 | Irving et al. |
| 2019/0192549 A1 | 6/2019 | Yoshikawa |

FOREIGN PATENT DOCUMENTS

| WO | WO-2018100558 A2 | 6/2018 |
| WO | WO-2018118664 A1 | 6/2018 |
| WO | WO-2019027857 A1 | 2/2019 |

OTHER PUBLICATIONS

Ager, C.R., et al., "Intratumoral Delivery of a Novel STING Agonist Synergizes With Checkpoint Blockade to Regress Multifocal Pancreatic Cancer" *Cancer Immunology Research* 7(2): Abstract A050, American Association for Cancer Research, United States (Feb. 2019).
(Continued)

*Primary Examiner* — Scarlett Y Goon
*Assistant Examiner* — Sarah Grace Scrivener
(74) *Attorney, Agent, or Firm* — Sterne, Kessler, Goldstein & Fox P.L.L.C.

(57) ABSTRACT

The present disclosure provides methods, pharmaceutical compositions, and kits for treating cancer in patients in need thereof. The methods comprise administering to a patient in need a STING (stimulator of interferon genes) agonist, such as Compound No. 14, or a pharmaceutically acceptable salt thereof, in combination with one or more checkpoint inhibitors. Suitable checkpoint inhibitors include anti-PD-1 antibodies, anti-PD-L1 antibodies and anti-CTLA-4 antibodies. Also provided are medicaments for use in treating cancer. Compound No. 14 has the structure:
(Continued)

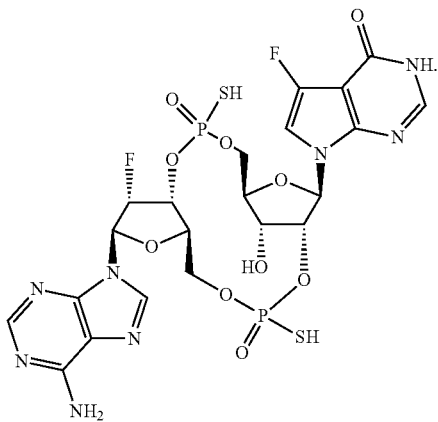

19 Claims, 10 Drawing Sheets

Related U.S. Application Data filed on Dec. 6, 2019, provisional application No. 62/872,039, filed on Jul. 9, 2019.

(58) Field of Classification Search
CPC ............ A61K 39/395; A61K 2039/505; A61K 2300/00; A61P 35/00
See application file for complete search history.

(56) References Cited

OTHER PUBLICATIONS

Barber, G.N., "STING-Dependent Cytosolic DNA Sensing Pathways," *Trends in Immunology* 35(2):88-93, Elsevier Science Ltd, England (2014).
Berge, S.M., et al., "Pharmaceutical Salts," *Journal of Pharmaceutical Sciences* 66(1):1-19, Wiley, United States (1977).
Blank, C., et al., "Interaction of PD-L1 on Tumor Cells with PD-1 on Tumor-specific T Cells as a Mechanism of Immune Evasion: Implications for Tumor Immunotherapy," *Cancer Immunology Immunotherapy* 54(4):307-314, Springer-Verlag, Germany (2005).
Deng, L., et al., "STING-Dependent Cytosolic DNA Sensing Promotes Radiation-Induced Type I Interferon-Dependent Antitumor Immunity in Immunogenic Tumors," *Immunity* 41(5):843-852, Cell Press, United States (2014).
Dubensky, T.W., et al., "Rationale, Progress and Development of Vaccines Utilizing STING-Activating Cyclic Dinucleotide Adjuvants," *Therapeutic Advances in Vaccines* 1(4):131-143, Sage Publications, England (2013).
Freeman, G.J., et al., "Engagement of the PD-1 Immunoinhibitory Receptor by a Novel B7 Family Member Leads to Negative Regulation of Lymphocyte Activation," *The Journal of Experimental Medicine* 192(7):1027-1034, The Rockefeller University Press, United States (2000).
Gao, J., et al., "Identification and Characterization of Phosphodiesterases that Specifically Degrade 3' 3'-Cyclic GMP-AMP," *Cell Research* 25(5):539-550, Nature Publishing Group, England (2015).
GenBank, "programmed cell death 1 ligand 1 isoform a precursor [*Homo sapiens*]," Accession No. NP_054862.1, accessed at https://www.ncbi.nlm.nih.gov/protein/NP_054862.
GenBank Accession No. AAL07473.1, accessed at https://www.ncbi.nlm.nih.gov/protein/AAL07473.
GenBank Accession No. AF414120.1, accessed at https://www.ncbi.nlm.nih.gov/nuccore/AF414120.1.
Grosso, J.F. and Jure-Kunkel, M.N., "CTLA-4 Blockade in Tumor Models: An Overview of Preclinical and Translational Research," *Cancer Immunity* 13:5, Cancer Research Institute, United States (2013).
Harrington, K.J., et al., "Preliminary Results of the First-In-Human (FIH) Study of MK-1454, an Agonist of Stimulator of Interferon Genes (STING), as Monotherapy or in Combination With Pembrolizumab (Pembro) in Patients With Advanced Solid Tumors or Lymphomas," *Developmental Therapeutics* 29(8):VIII712, Elsevier Inc, Netherlands (Oct. 2018).
International Search Report and Written Opinion for International Application No. PCT/IB2020/056440, European Patent Office, Netherlands, mailed on Oct. 8, 2020, 13 pages.
Li, L., et al., "Hydrolysis of 2' 3'-cGAMP by ENPP1 and Design of Nonhydrolyzable Analogs," *Nat Chem Biol* 10(12):1043-1048, Nature Pub. Group, United States (2014).
Meehan, R.E., et al., "Nuclease-Resistant c-di-AMP Derivatives That Differentially Recognize RNA and Protein Receptors," *Biochemistry* 55(6):837-849, American Chemical Society, United States (2016).
Nielsen, C., et al., "Alternative Splice Variants of the Human Pd-1 Gene," *Cellular Immunology* 235(2):109-116, Elsevier, Netherlands (2005).
Perera, S.A., et al., "Combination With a Novel STING Agonist Significantly Improves Efficacy of Anti-PD1 Therapy in Mouse Syngeneic Tumor Models," *Cancer Immunology Research Checkpoints and Immunomodulation* 6(9):Abstract A08, American Association for Cancer Research, United States (Sep. 2018).
Wolfson, W., "Amber Codon Flashing Ambrx Augments Proteins With Unnatural Amino Acids," *Chemistry & Biology* 13(10):1011-1012, Elsevier, United States (2006).
Woo, S.R., et al., "STING-Dependent Cytosolic DNA Sensing Mediates Innate Immune Recognition of Immunogenic Tumors," *Immunity* 41(5):830-842, Cell Press, United States (2014).

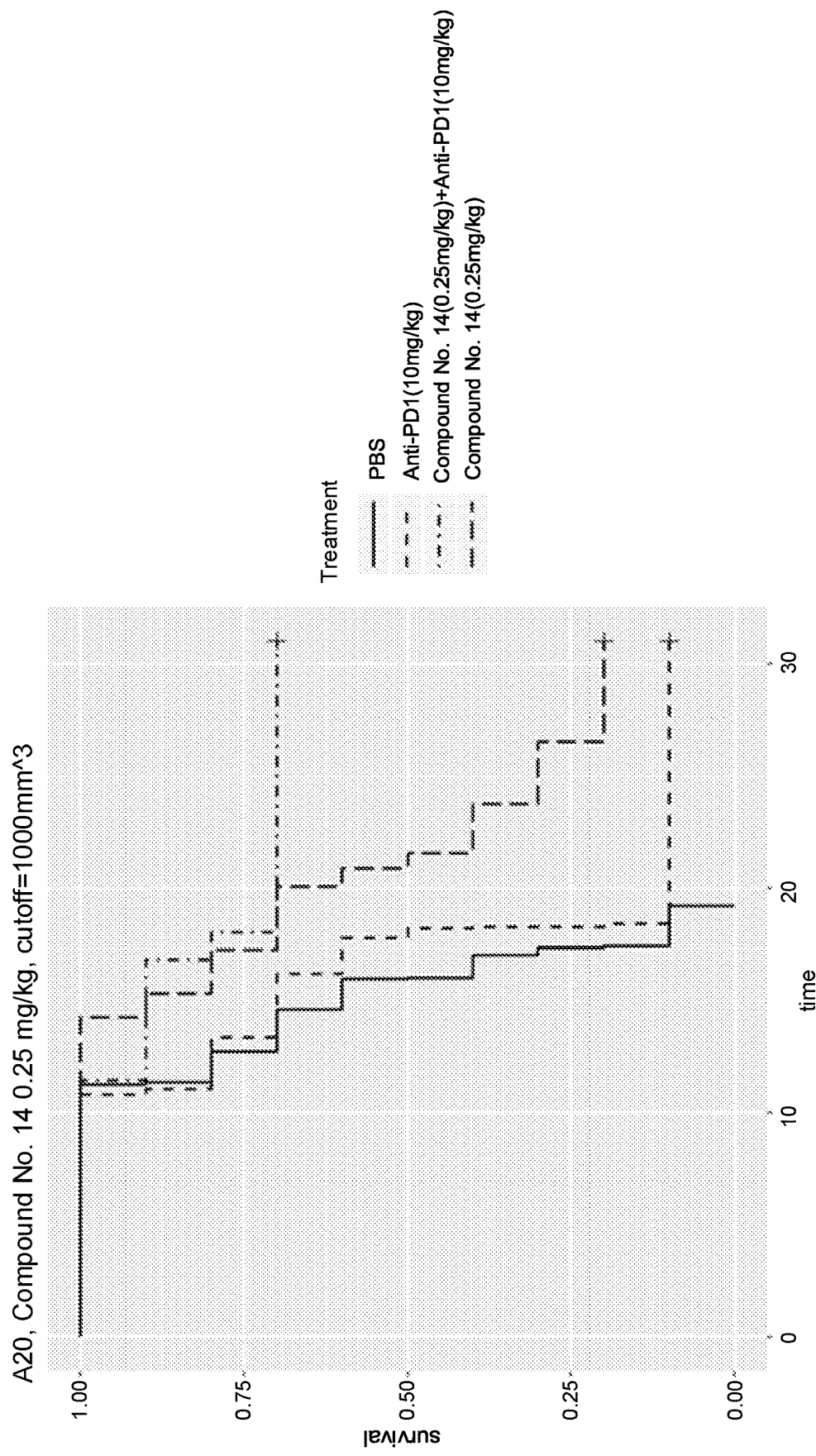
FIG. 1a: Progression-free survival Kaplan-Meier curves of vehicle, Compound No. 14, anti-mPD-1, and combination in mouse A20 syngeneic tumor model

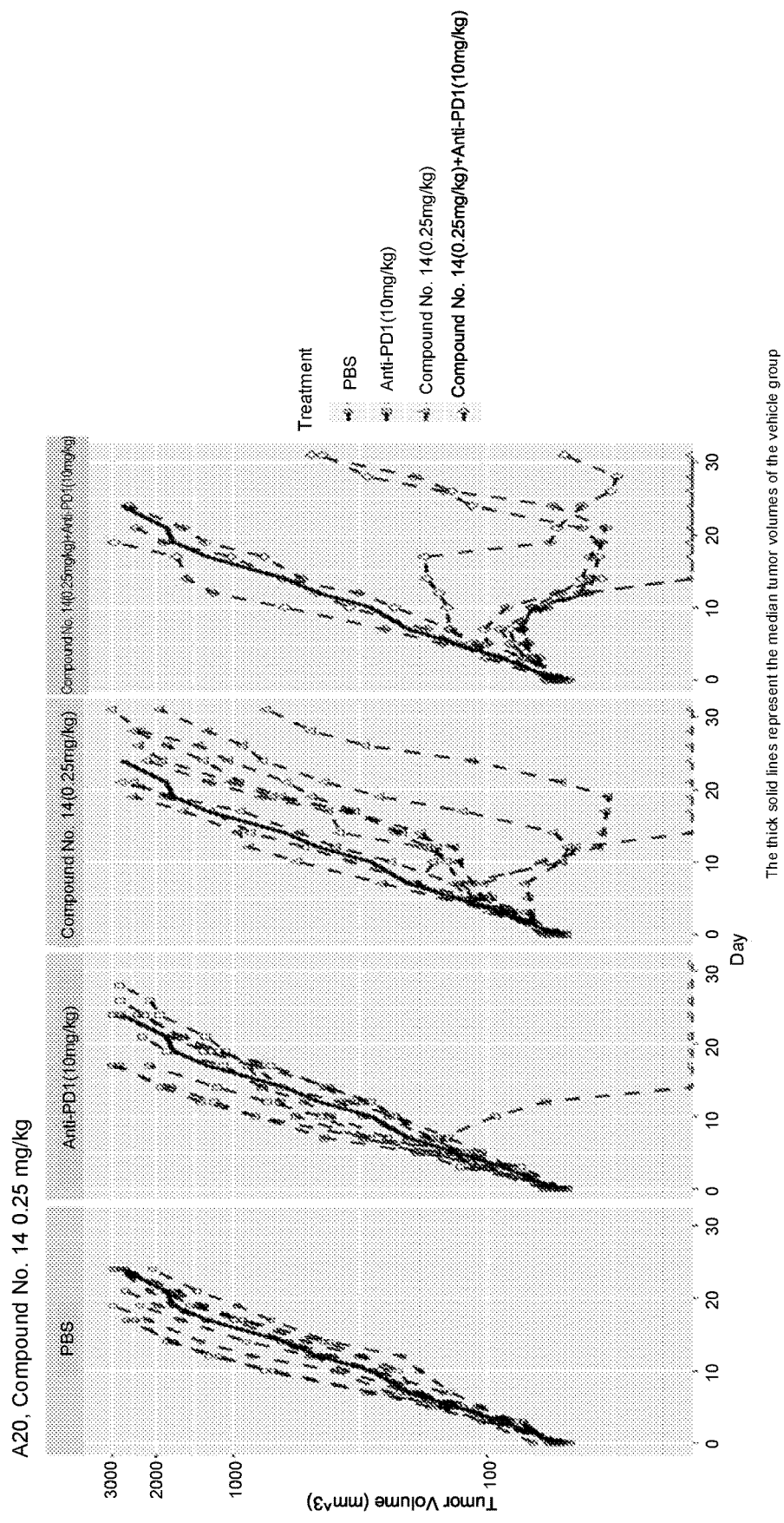
FIG. 1b: Tumor growth curves of vehicle, Compound No. 14, anti-mPD-1, and combination in mouse A20 syngeneic tumor model

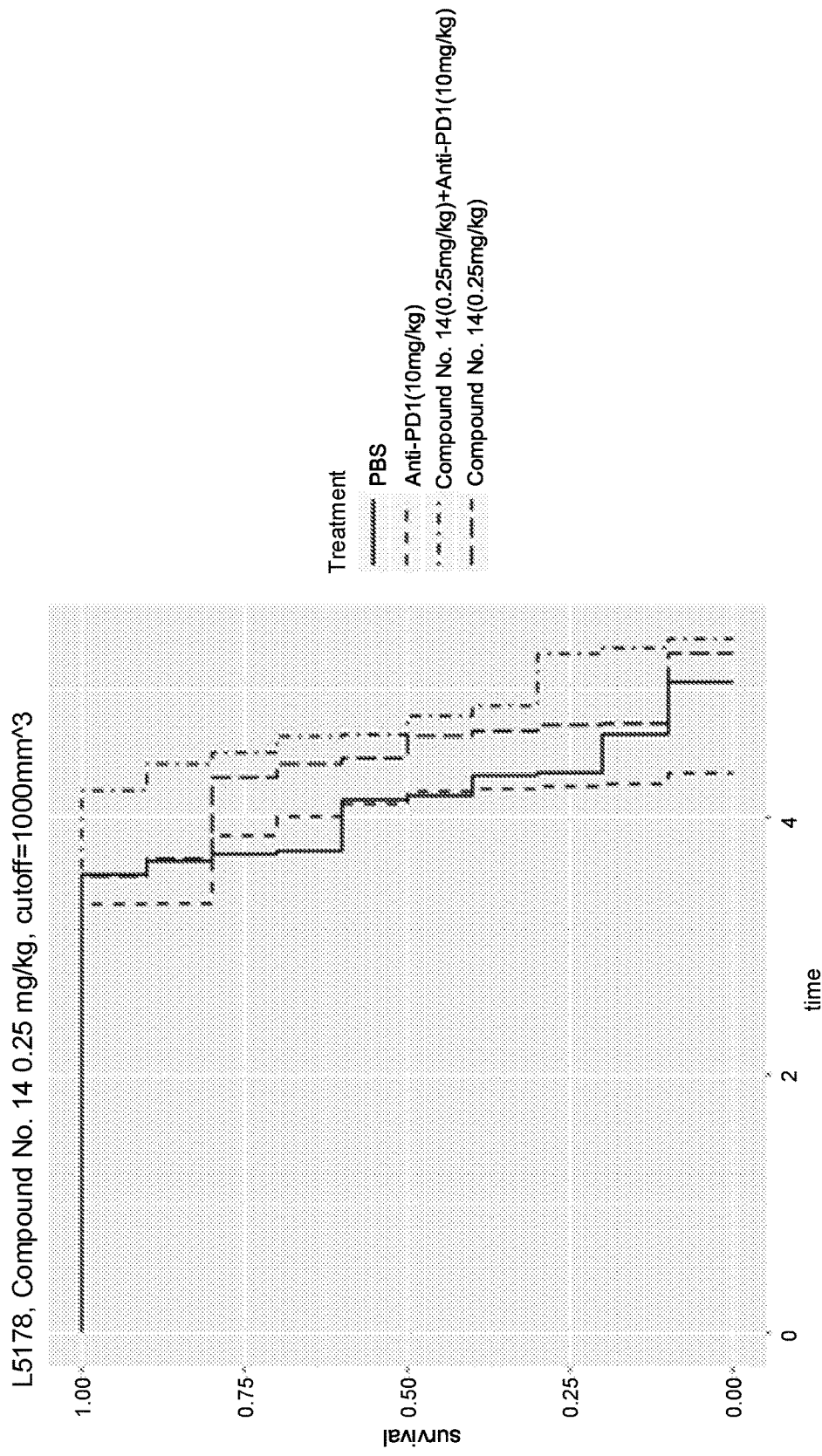
FIG. 2a: Progression-free survival Kaplan-Meier curves of vehicle, Compound No. 14, anti-mPD-1, and combination in mouse L5178-R syngeneic tumor model

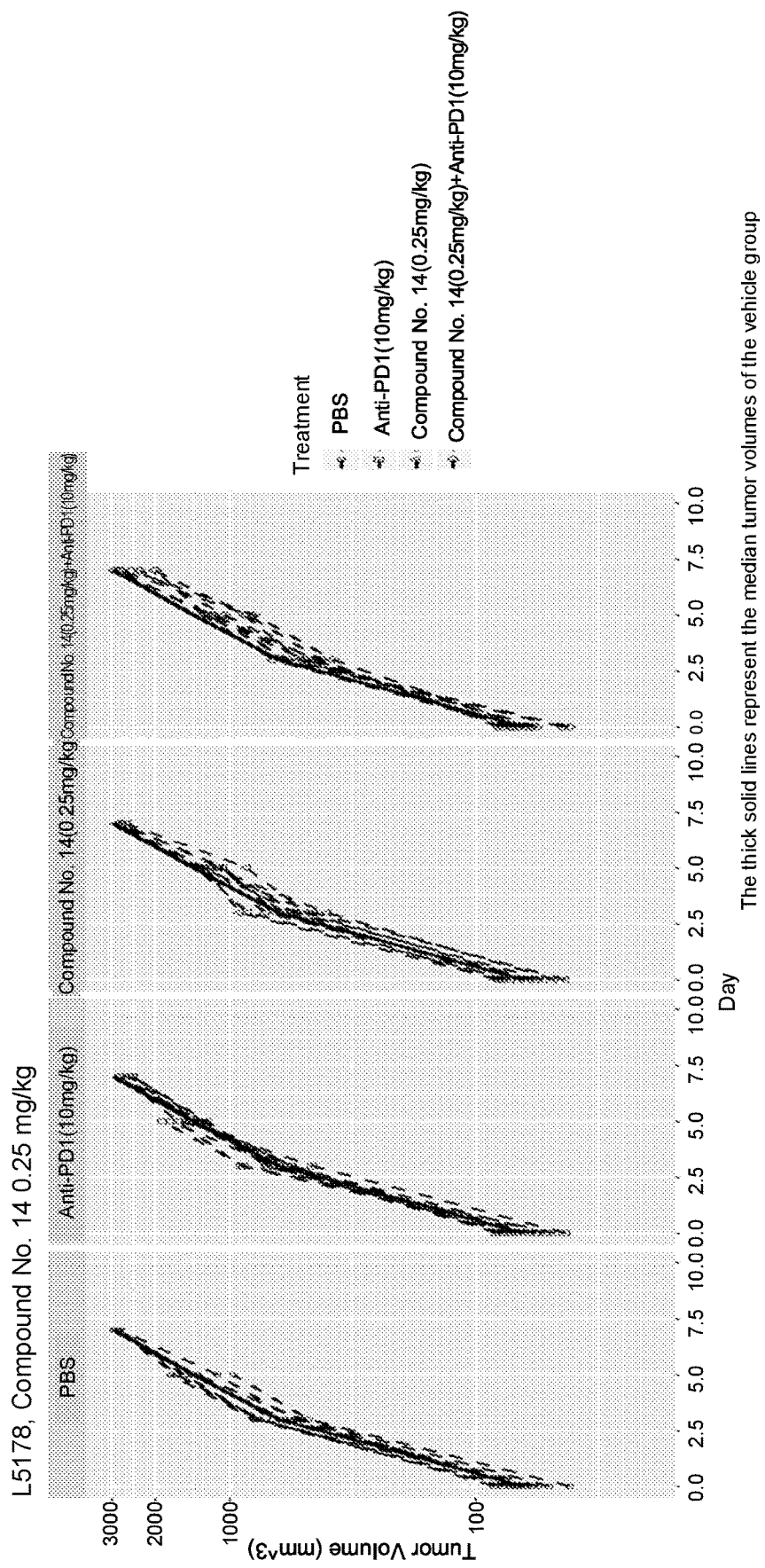
FIG. 2b: Tumor growth curves of vehicle, Compound No. 14, anti-mPD-1, and combination in mouse L5178-R syngeneic tumor model

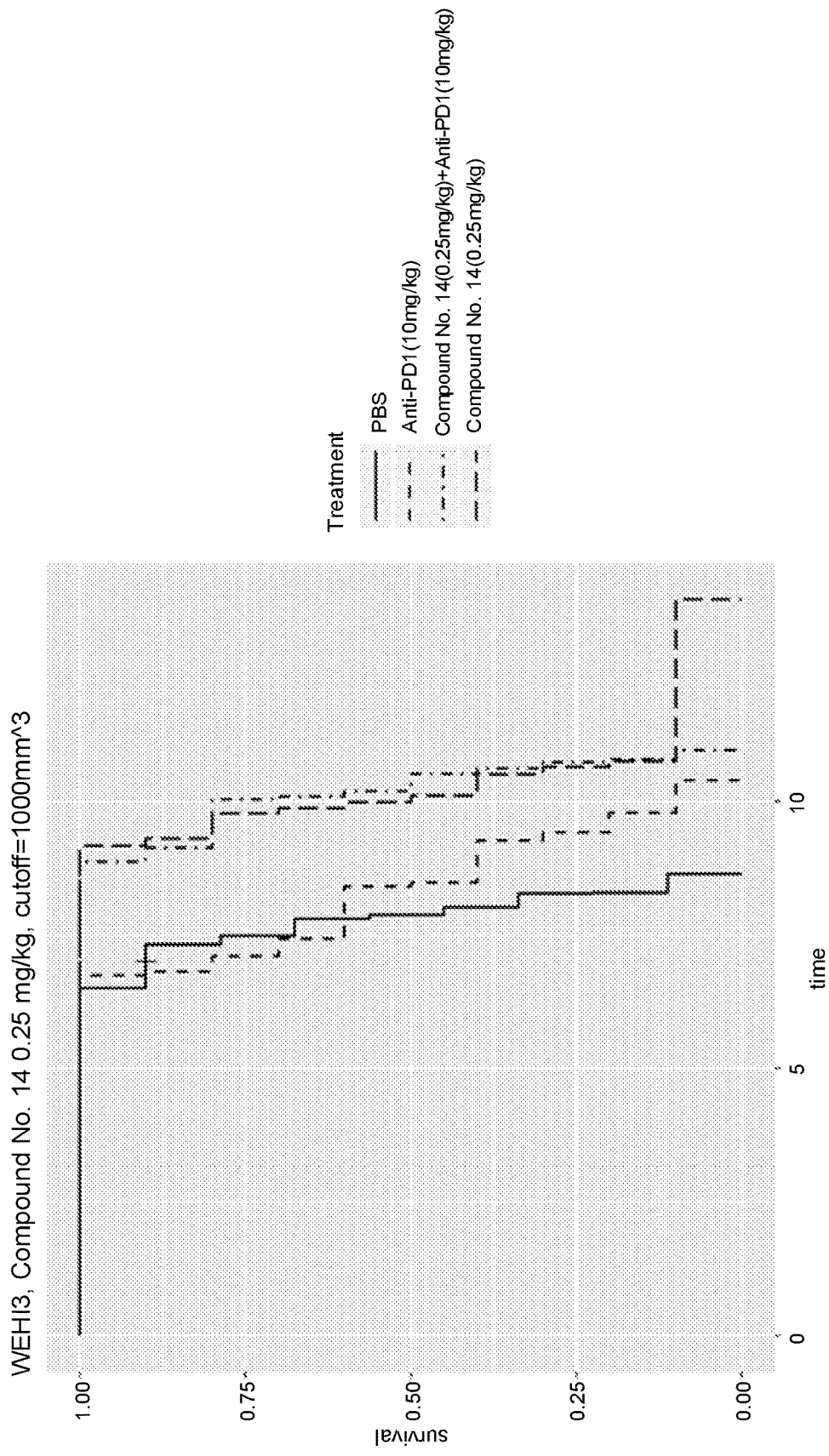
FIG. 3a: Progression-free survival Kaplan-Meier curves of vehicle, Compound No. 14, anti-mPD-1, and combination in mouse WEHI-3 syngeneic tumor model

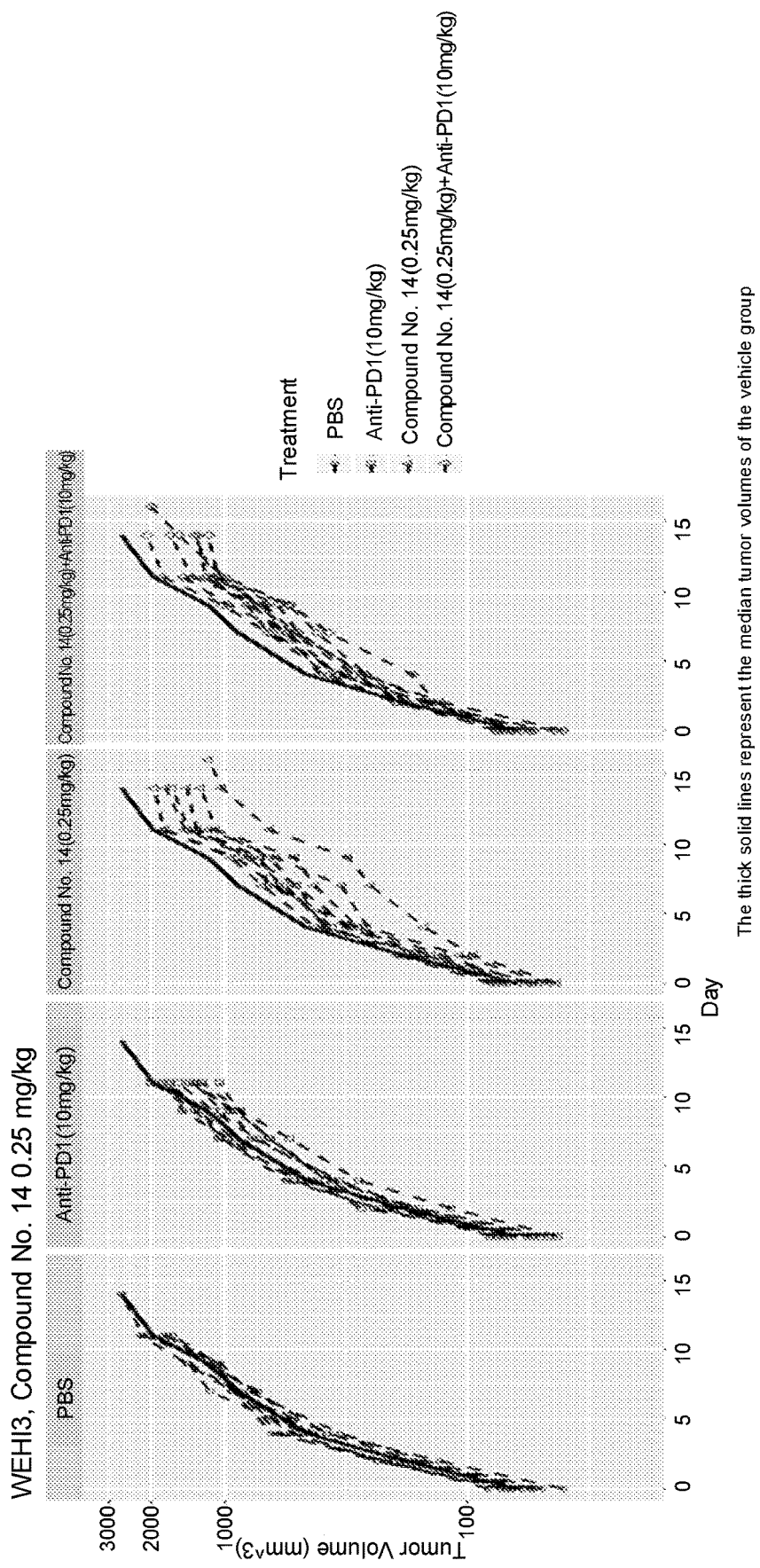
FIG. 3b: Tumor growth curves of vehicle, Compound No. 14, anti-mPD-1, and combination in mouse WEHI-3 syngeneic tumor model

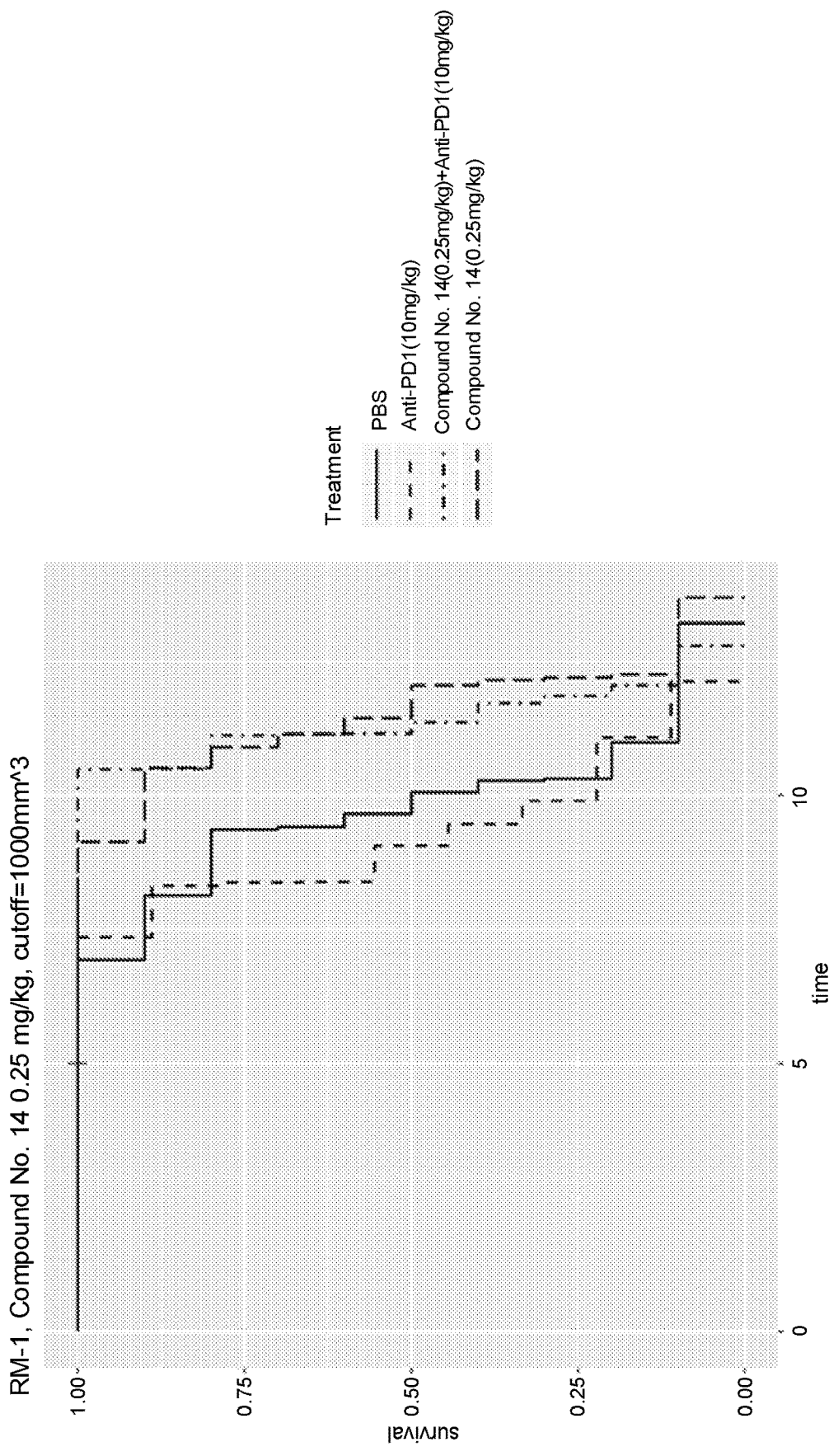
FIG. 4a: Progression-free survival Kaplan-Meier curves of vehicle, Compound No. 14, anti-mPD-1, and combination in mouse RM-1 syngeneic tumor model

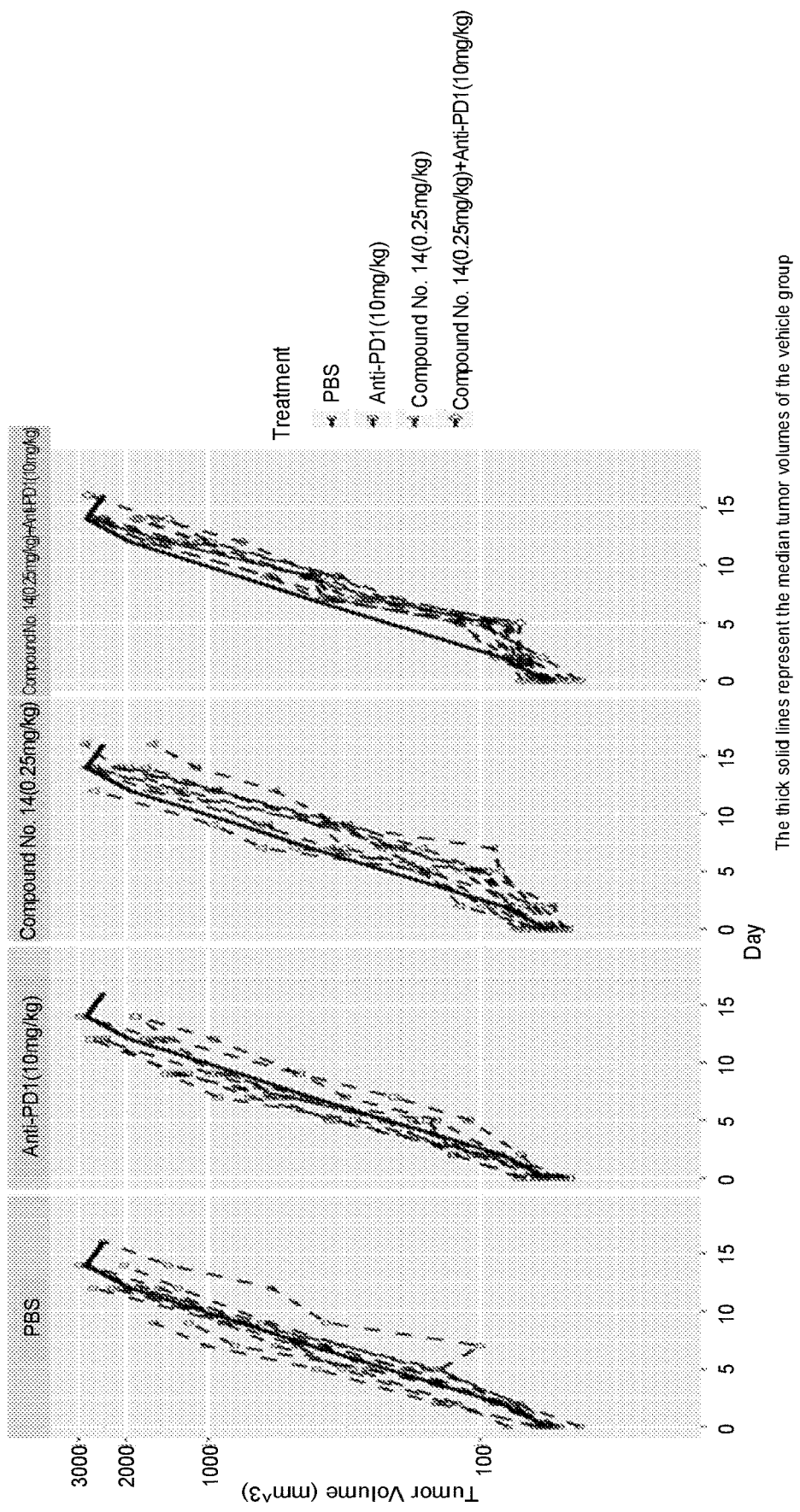
FIG. 4b: Tumor growth curves of vehicle, Compound No. 14, anti-mPD-1, and combination in mouse RM-1 syngeneic tumor model RM-1, Compound No. 14 0.25 mg/kg

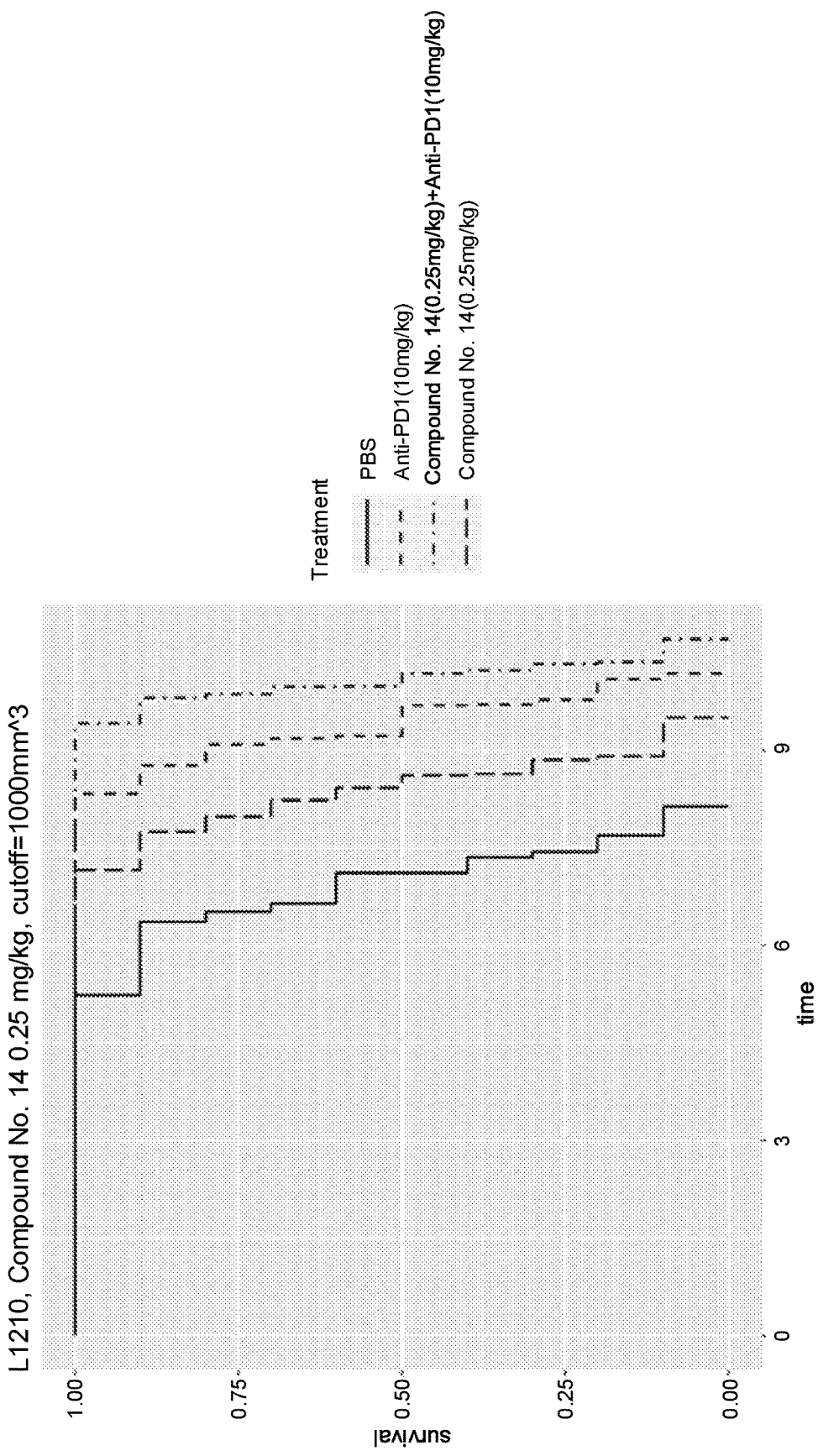
FIG. 5a: Progression-free survival Kaplan-Meier curves of vehicle, Compound No. 14, anti-mPD-1, and combination in mouse L1210 syngeneic tumor model

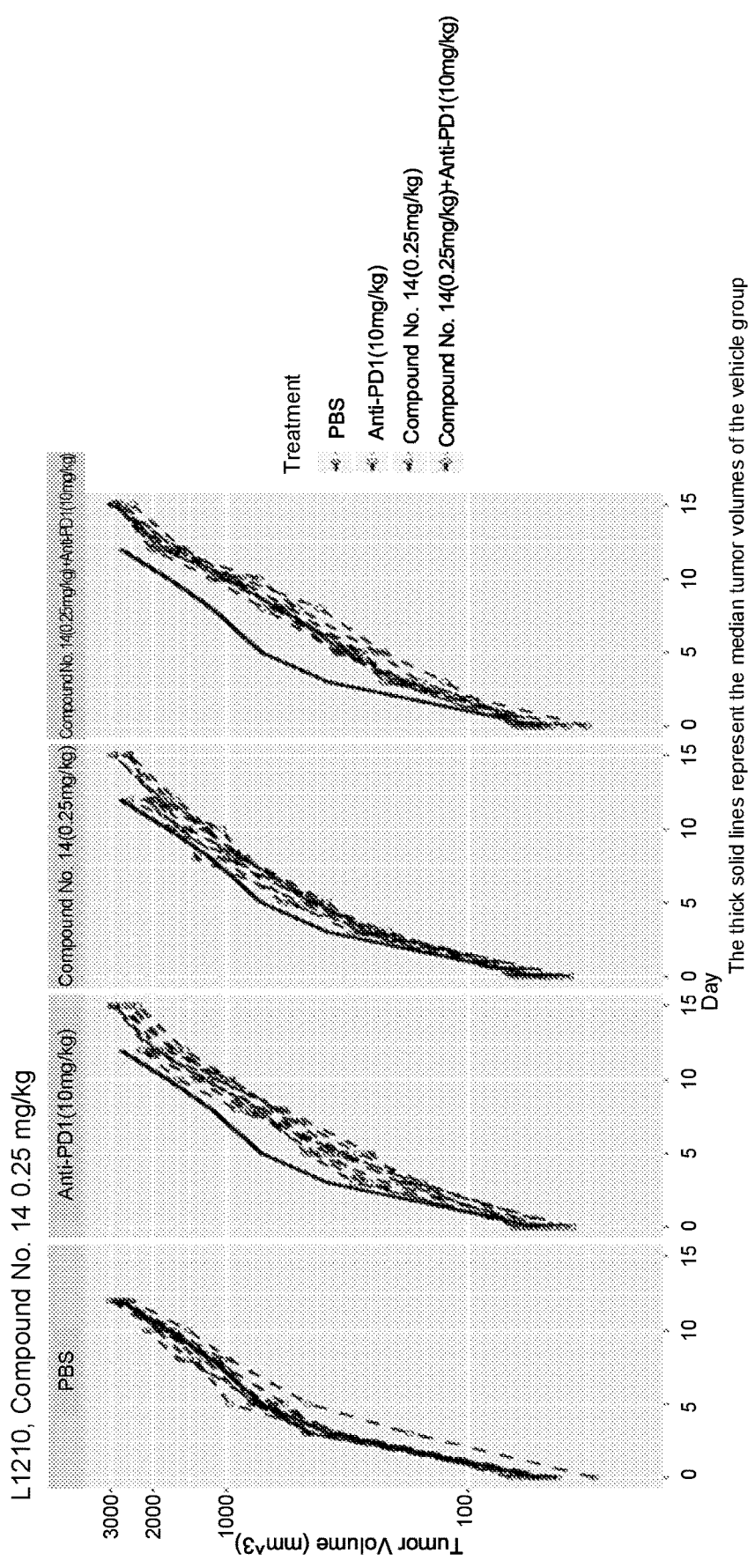
FIG. 5b: Tumor growth curves of vehicle, Compound No. 14, anti-mPD-1, and combination in mouse L1210 syngeneic tumor model

ADMINISTRATION OF STING AGONIST AND CHECKPOINT INHIBITORS

FIELD

The present disclosure relates to methods of treating cancer. In particular, the present disclosure provides methods for treating various cancers by administering a STING (stimulator of interferon genes) agonist in combination with one or more checkpoint inhibitors.

BACKGROUND

In 2012, there were an estimated 14 million cases of cancer diagnosed worldwide and about 8.2 million deaths. The global cancer burden is growing at an alarming pace; in 2030 alone, about 21.3 million new cancer cases and 13.1 million cancer deaths are expected to occur, simply due to the growth and aging of the population. Cancer is the second most common cause of death in the United States, exceeded only by heart disease, accounting for nearly one of every four deaths. The National Cancer Institute estimates that approximately 14.5 million Americans with a history of cancer were alive in 2014. Some of these individuals were cancer free, while others still had evidence of cancer and may have been undergoing treatment. Although medical advances have improved cancer survival rates, there is a continuing need for new and more effective treatment.

Cancer treatments have mainly relied on the surgery, radiotherapy, cytotoxic chemotherapies and combinations thereof. Within the last decade, however, targeted cancer therapies have opened a new era in the field of oncology. Targeted cancer therapies are drugs designed to interfere with specific molecules necessary for tumor growth and progression, and can include small molecules and larger chemical entities, such as monoclonal antibodies (mAbs).

STING is a transmembrane receptor localized to the ER that recognizes and binds cyclic dinucleotides. The natural ligands recognized by STING include bacteria/protozoa-derived cyclic dinucleotides (CDNs), 2',3'-cGAMP synthesized by the upstream cGAS (cyclic GMP-AMP synthase), and the like. See *Trends in Immunology* 35:88-93 (2014). It is reported that 2',3'-cGAMP, which is one of the natural ligands, is decomposed by ENPP1 (ecto-nucleotide-pyrophosphatase/phosphodiesterase), which is a pyrophosphatase/phosphodiesterase, and that the other CDNs are decomposed by other phosphodiesterases. See *Nat Chem Biol* 10:1043-1048 (2014); *Cell Res* 25:539-550 (2015); *Biochemistry* 55:837-849 (2016). STING activation by these natural ligands induces the phosphorylation of TBK1 (TANK binding kinase 1) and IRF3 (Interferon regulatory factor 3), leading to the activation of NFkB and a type-I-interferon (IFN) response, respectively. See *Trends in Immunology* 35:88-93 (2014).

The effects of STING on cancer cell growth control were demonstrated using genetically modified mice. It was reported that STING-deficient and IRF3-deficient mice show uncontrolled tumor growth, compared to wild-type mice. See *Immunity* 41: 830-842 (2014). In addition, it is also reported that the cancer cell growth in a tumor-allografted mouse was suppressed by radiation therapy, but in mice genetically deficient for STING and IFNAR1 (interferon (alpha and beta) receptor 1, receptor of type-I IFN produced by the downstream signal), the effect of the radiation therapy was reduced. See *Immunity* 41:843-852 (2014). Taking the above mentioned evidence together, STING is considered to play a critical role in suppressing cancer cell growth. Therefore, STING agonists can be used as anticancer agents. In addition, the activation of STING can further potentiate the immune effect of traditional vaccines, due to STING's ability to activate both innate and adaptive immunity. See *Ther Adv Vaccines* 1:131-143 (2013). Therefore, STING agonists can also be used as an adjuvant for various vaccines.

In addition to small molecules, targeted therapies can include monoclonal antibodies. For example, among the many known monoclonal antibody targeted therapies are monoclonal antibodies to PD-1 (e.g., nivolumab/Opdivo®, and) pembrolizumab/Keytruda®), monoclonal antibodies to PD-L1 (e.g., atezolizumab/Tecentriq®, durvalumab/Imfinzi®, and avelumab/Bavencio®), and monoclonal antibodies to CTLA-4 (e.g., ipilimumab/Yervoy®). Thus, some cancers may be PD-1-mediated disorders, PD-L1-mediated disorders, and CTLA-4-mediated disorders. Additional monoclonal antibody targeted therapies include, but are not limited to, monoclonal antibodies to CD20 (e.g. rituximab/Rituxan®) CD52 (e.g., alemtuzumab/Campath®), VEGF (e.g., bevacizumab/Avastin®), HER2 (e.g., trastuzumab/Herceptin® for treating Her2+ breast and stomach cancers), and EGFR (e.g., cetuximab/Erbitux® for treating colorectal cancer).

New combinations of therapeutic agents that provide a beneficial effect in the treatment of cancers are desirable in order to prolong patient's lives while maintaining a high quality of life. New combinations may provide an increased benefit as compared to each of the agents alone. In particular, combined treatment regimens may be helpful for patients suffering from disease conditions including proliferative disorders, autoimmune diseases, inflammatory diseases, fibrotic diseases and kidney diseases, and could potentially even decrease the rate of relapse or overcome the resistance to a particular anticancer agent sometimes seen in these patients. This is especially true in the case where the cancers may be resistant or refractory to currently available therapeutic regimens.

Thus, there is a need for new cancer treatment regimens, including combination therapies.

SUMMARY

In one aspect, the present disclosure relates to methods of treating cancer comprising administering a STING agonist and a checkpoint inhibitor in combination to a subject in need of such treatment.

In one aspect, the present disclosure relates to methods of treating a patient having cancer, comprising administering to a patient in need of said treating a combination of Compound No. 14, having the following structure:

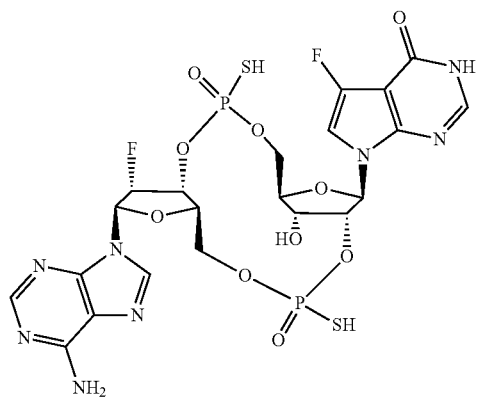 [SMILES: Nc1ncnc2c1ncn2[C@@H]1O[C@@H]2COP(=O)(S)O[C@@H]3[C@H](O)[C@@H](COP(=O)(S)O[C@H]2[C@H]1F)O[C@H]3n1cc(F)c2c(=O)[nH]cnc21]

or a pharmaceutically acceptable salt thereof, and a checkpoint inhibitor.

In some embodiments, the checkpoint inhibitor is selected from the group consisting of anti-PD-1 antibodies, anti-PD-L1 antibodies, and anti-CTLA-4 antibodies.

In some embodiments, the checkpoint inhibitor is an anti-PD-1 antibody.

In some embodiments, the anti-PD-1 antibody is selected from the group consisting of nivolumab, pembrolizumab, lambrolizumab, pidilizumab, BMS-936559, and AMP-224.

In some embodiments, the checkpoint inhibitor is an anti-PD-L1 antibody.

In some embodiments, the anti-PD-L1 antibody is selected from the group consisting of atezolizumab, durvalumab, avelumab, YW243.55.S70, MEDI-4736, MSB-0010718C, LY3300054, BMS-936559, MPDL3280A, and MDX-1105.

In some embodiments, the checkpoint inhibitor is an anti-CTLA-4 antibody.

In some embodiments, the anti-CTLA-4 antibody is selected from the group consisting of ipilimumab and tremelimumab.

In some embodiments, Compound No. 14 or a pharmaceutically acceptable salt thereof, is administered orally.

In some embodiments, Compound No. 14 or a pharmaceutically acceptable salt thereof, is administered intravenously.

In some embodiments, Compound No. 14 or a pharmaceutically acceptable salt thereof, is administered by intravenous infusion.

In some embodiments, the checkpoint inhibitor is administered intravenously.

In some embodiments, the checkpoint inhibitor is administered by intravenous infusion.

In some embodiments, the checkpoint inhibitor is administered by subcutaneous injection.

In some embodiments, the checkpoint inhibitor is administered subcutaneously.

In some embodiments, Compound No. 14 and the checkpoint inhibitor are administered concurrently.

In some embodiments, Compound No. 14 and the checkpoint inhibitor are administered sequentially in separate pharmaceutical compositions.

In some embodiments, the cancer is a PD-1 positive cancer, a PD-L1 positive cancer, or a CTLA-4 positive cancer.

In some embodiments, the cancer is a solid tumor or a hematological malignancy. In some embodiments, the cancer is a metastatic solid tumor. In some embodiments, the cancer is an advanced solid tumor.

In some embodiments, the cancer is melanoma, lung cancer, renal cancer, lymphoma, head and neck cancer, urothelial cancer, prostate cancer, bladder cancer, breast cancer, gastric cancer, colorectal cancer, leukemia, cervical cancer, microsatellite instability-high cancer, hepatocellular carcinoma, or Merkel cell carcinoma.

In some embodiments, the melanoma is metastatic melanoma, unresectable melanoma, or cutaneous melanoma.

In some embodiments, the lung cancer is non-small cell lung cancer or small cell lung cancer.

In some embodiments, the non-small cell lung cancer is metastatic non-small cell lung cancer, metastatic squamous non-small cell lung cancer, or metastatic nonsquamous non-small cell lung cancer.

In some embodiments, the renal cancer is renal cell carcinoma.

In some embodiments, the lymphoma is classical Hodgkin lymphoma or primary mediastinal large B-cell lymphoma.

In some embodiments, the head and neck cancer is head and neck squamous cell carcinoma.

In some embodiments, the urothelial cancer is urothelial carcinoma.

In some embodiments, the prostate cancer is hormone-refractory prostate cancer.

In some embodiments, the gastric cancer is gastroesophageal junction adenocarcinoma.

In some embodiments, the cancer is microsatellite instability-high cancer.

In some embodiments, Compound No. 14 or a pharmaceutically acceptable salt thereof, is administered once every two weeks, once every week, twice a week, three times a week, or daily.

In some embodiments, Compound No. 14 or a pharmaceutically acceptable salt thereof, is administered twice a week.

In some embodiments, Compound No. 14 or a pharmaceutically acceptable salt thereof, is administered once every week.

In some embodiments, Compound No. 14 or a pharmaceutically acceptable salt thereof, is administered on days 1, 4, 8, and 11 of a 21 day cycle.

In some embodiments, the checkpoint inhibitor is administered once every twelve weeks, once every four weeks, once every three weeks, once every two weeks, once every week, twice a week, three times a week, or daily.

In some embodiments, the checkpoint inhibitor is administered once every two weeks.

In some embodiments, the checkpoint inhibitor is administered once every three weeks.

In some embodiments, the checkpoint inhibitor is administered once every four weeks.

In some embodiments, the checkpoint inhibitor is administered once every twelve weeks.

In some embodiments, the checkpoint inhibitor is administered on Day 1 of a treatment cycle.

In some embodiments, the treatment cycle is 14 days, 21 days, 28 days, or 84 days.

In some embodiments, Compound No. 14, or a pharmaceutically acceptable salt thereof, and the checkpoint inhibitor are administered simultaneously once every twelve weeks, once every four weeks, once every three weeks, once every two weeks, once every week, twice a week, three times a week, daily, or on days 1, 4, 8, and 11 of a 21 day cycle.

In some embodiments, Compound No. 14, or a pharmaceutically acceptable salt thereof, is administered once every two weeks, once every week, twice a week, three times a week, daily, or on days 1, 4, 8, and 11 of a 21 day cycle; and the checkpoint inhibitor is separately administered once every twelve weeks, once every four weeks, once every three weeks, once every two weeks, once every week, twice a week, three times a week, or daily.

In one aspect, the present disclosure relates to a kit comprising a medicament for use in treating cancer in a subject in need of such treatment. The kit comprises a medicament comprising a STING agonist, and instructions for administering the STING agonist and the one or more checkpoint inhibitors; or the kit comprises a medicament comprising the one or more checkpoint inhibitors, and instructions for administering the one or more checkpoint inhibitors and a STING agonist. The kit can contain both a medicament comprising a STING agonist and a medicament comprising one or more checkpoint inhibitors, and instructions for administering the STING agonist and the one or more checkpoint inhibitors. The kit can also comprise one or more additional therapeutic agents.

In one aspect, the present disclosure relates to a medicament for use in treating cancer in a subject in need of such treatment. The medicament comprises a STING agonist and one or more checkpoint inhibitors. The medicament can also comprise one or more additional therapeutic agents.

BRIEF DESCRIPTION OF THE FIGURES

FIG. 1a shows a Progression-free survival Kaplan-Meier plot of survival as a function of time in a mouse A20 syngeneic tumor model following administration of Compound No. 14, an anti-mouse PD-1 antibody ("anti-mPD-1"), a combination of Compound No. 14 and an anti-mPD-1, and vehicle to mice.

FIG. 1b shows a plot of individual tumor volume as a function of time in a mouse A20 syngeneic tumor model following administration of Compound No. 14, an anti-mPD-1, a combination of Compound No. 14 and an anti-mPD-1, and vehicle to mice.

FIG. 2a shows a Progression-free survival Kaplan-Meier plot of survival as a function of time in a mouse L5178-R syngeneic tumor model following administration of Compound No. 14, an anti-mPD-1, a combination of Compound No. 14 and an anti-mPD-1, and vehicle to mice.

FIG. 2b shows a plot of individual tumor volume as a function of time in a mouse L5178-R syngeneic tumor model following administration of Compound No. 14, an anti-mPD-1, a combination of Compound No. 14 and an anti-mPD-1, and vehicle to mice.

FIG. 3a shows a Progression-free survival Kaplan-Meier plot of survival as a function of time in a mouse WEHI-3 syngeneic tumor model following administration of Compound No. 14, an anti-mPD-1, a combination of Compound No. 14 and an anti-mPD-1, and vehicle to mice.

FIG. 3b shows a plot of individual tumor volume as a function of time in a mouse WEHI-3 syngeneic tumor model following administration of Compound No. 14, an anti-mPD-1, a combination of Compound No. 14 and an anti-mPD-1, and vehicle to mice.

FIG. 4a shows a Progression-free survival Kaplan-Meier plot of survival as a function of time in a mouse RM-1 syngeneic tumor model following administration of Compound No. 14, an anti-mPD-1, a combination of Compound No. 14 and an anti-mPD-1, and vehicle to mice.

FIG. 4b shows a plot of individual tumor volume as a function of time in a mouse RM-1 syngeneic tumor model following administration of Compound No. 14, an anti-mPD-1, a combination of Compound No. 14 and an anti-mPD-1, and vehicle to mice.

FIG. 5a shows a Progression-free survival Kaplan-Meier plot of survival as a function of time in a mouse L1210 syngeneic tumor model following administration of Compound No. 14, an anti-mPD-1, a combination of Compound No. 14 and an anti-mPD-1, and vehicle to mice.

FIG. 5b shows a plot of individual tumor volume as a function of time in a mouse L1210 syngeneic tumor model following administration of Compound No. 14, an anti-mPD-1, a combination of Compound No. 14 and an anti-mPD-1, and vehicle to mice.

DETAILED DESCRIPTION

Definitions and Abbreviations

To facilitate an understanding of the present disclosure, a number of abbreviations, terms, and phrases are defined below.

AUC area under the plasma concentration versus time curve
BSA body surface area
CR complete response
MTD maximum tolerated dose
STING stimulator of interferon genes
PR partial response
BIW twice weekly
QW once weekly
Q2W once every 2 weeks
QD once daily
Q Every
NSCLC non-small cell lung cancer
SCLC small cell lung cancer Unless defined otherwise, all technical and scientific terms used herein have the same meaning as is commonly understood by one of skill in the art to which this disclosure belongs. All patents and publications referred to herein are incorporated by reference in their entirety.

As used herein, the term "cancer" refers to a cellular disorder characterized by uncontrolled or dysregulated cell proliferation, decreased cellular differentiation, inappropriate ability to invade surrounding tissue, and/or ability to establish new growth at ectopic sites. The term "cancer" includes solid tumors and non-solid tumors, such as, for example, hematological tumors. The term "cancer" encompasses diseases of skin, tissues, organs, bone, cartilage, blood, and vessels. The term "cancer" further encompasses primary and metastatic cancers.

As used herein, the term "autoimmune disease" refers to a disorder arising from an abnormal immune response to a normal body part. The term "autoimmune disease" encompasses disorders including, but not limited to, Rheumatoid Arthritis (RA), Granulomatosis with Polyangiitis (GPA) (Wegener's Granulomatosis), and Microscopic Polyangiitis (MPA).

The term "PD-1" (also known as programmed cell death protein 1, PDCD1, CD279, SLEB2, or SLE1) refers to any native PD-1, unless otherwise indicated. The term "PD-1" encompasses "full-length," unprocessed PD-1 as well as any form of PD-1 that results from processing within the cell. The term also encompasses naturally occurring variants of PD-1, e.g., splice variants, allelic variants, and isoforms.

The term "PD-L1" (also known as programmed cell death 1 ligand) refers to any native PD-L1, unless otherwise indicated. The term "PD-L1" encompasses "full-length," unprocessed PD-L1 as well as any form of PD-L1 that results from processing within the cell. The term also encompasses naturally occurring variants of PD-L1, e.g., splice variants, allelic variants, and isoforms.

The term "CTLA-4" (also known as cytotoxic T-lymphocyte-associated antigen 4) refers to any native CTLA-4, unless otherwise indicated. The term "CTLA-4" encompasses "full-length," unprocessed CTLA-4 as well as any form of CTLA-4 that results from processing within the cell. The term also encompasses naturally occurring variants of CTLA-4, e.g., splice variants, allelic variants, and isoforms.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

A "blocking" antibody or an "antagonist" antibody is one which inhibits or reduces biological activity of the antigen it binds, such as, e.g., PD-1, PD-L1, or CTLA-4. In a certain embodiment, blocking antibodies or antagonist antibodies substantially or completely inhibit the biological activity of the antigen. Desirably, the biological activity is reduced by 10%, 20%, 30%, 50%, 70%, 80%, 90%, 95%, or even 100%.

The term "anti-PD-1 antibody" or "an antibody that binds to PD-1" refers to an antibody that is capable of binding PD-1 with sufficient affinity such that the antibody is useful as a diagnostic and/or therapeutic agent in targeting PD-1. The extent of binding of an anti-PD-1 antibody to an unrelated, non-PD-1 protein is less than about 10% of the binding of the antibody to PD-1 as measured, e.g., by a radioimmunoassay (MA). In certain embodiments, an antibody that binds to PD-1 has a dissociation constant (Kd) of ≤1 µM, ≤100 nM, ≤10 nM, ≤1 nM, or ≤0.1 nM.

The term "anti-PD-L1 antibody" or "an antibody that binds to PD-L1" refers to an antibody that is capable of binding PD-L1 with sufficient affinity such that the antibody is useful as a diagnostic and/or therapeutic agent in targeting PD-L1. The extent of binding of an anti-PD-L1 antibody to an unrelated, non-PD-L1 protein is less than about 10% of the binding of the antibody to PD-L1 as measured, e.g., by a radioimmunoassay (MA). In certain embodiments, an antibody that binds to PD-L1 has a dissociation constant (Kd) of ≤1 µM, ≤100 nM, ≤10 nM, ≤1 nM, or ≤0.1 nM.

The term "anti-CTLA-4 antibody" or "an antibody that binds to CTLA-4" refers to an antibody that is capable of binding CTLA-4 with sufficient affinity such that the antibody is useful as a diagnostic and/or therapeutic agent in targeting CTLA-4. The extent of binding of an anti-CTLA-4 antibody to an unrelated, non-CTLA-4 protein is less than about 10% of the binding of the antibody to CTLA-4 as measured, e.g., by a radioimmunoassay (MA). In certain embodiments, an antibody that binds to CTLA-4 has a dissociation constant (Kd) of ≤1 µM, ≤100 nM, ≤10 nM, ≤1 nM, or ≤0.1 nM.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species.

As used herein, the term "effective amount" or "therapeutically effective amount" refers to an amount of a compound, or combination of one or more compounds that, when administered (either sequentially or simultaneously) elicits the desired biological or medicinal response, e.g., either destroys the target cancer cells or slows or arrests the progression of the cancer in a patient. The therapeutically effective amount may vary depending upon the intended application (in vitro or in vivo), or the patient and disease condition being treated, e.g., the weight and age of the patient, the severity of the disease condition, the manner of administration and the like, which may readily be determined by one skilled in the art. The term also applies to a dose that will induce a particular response in target cells, e.g., reduction of platelet adhesion and/or cell migration. For example, in some embodiments, the "therapeutically effective amount" as used herein refers to the amount of Compound No. 14 or a pharmaceutically acceptable salt thereof, and the amount of checkpoint inhibitor that, when administered separately or in combination, have a beneficial effect. In some embodiments, the combined effect is additive. In some embodiments, the combined effect is synergistic. Further, it will be recognized by one skilled in the art that in the case of combination therapy, the amount of Compound No. 14 or a pharmaceutically acceptable salt thereof and/or the amount of the checkpoint inhibitor may be used in a "subtherapeutic amount", i.e., less than the therapeutically effective amount of Compound No. 14 or a pharmaceutically acceptable salt thereof, or the checkpoint inhibitor alone.

In any form or composition, the administered dose(s) or the therapeutically effective (total) amount may be expressed as amount(s) of therapeutic substance(s) per patient as either based on (i) BSA, e.g., as mg/m$^2$, or (ii) amount, e.g., as mg.

The term "about" refers to approximately, in the region of, roughly, or around. When the term "about" is used in conjunction with a number or a numerical range, it means that the number or numerical range referred to is an approximation within experimental variability (or within statistical experimental error), and thus the number or numerical range may vary from, for example, between 1% and 15% of the stated number or numerical range. In general, the term "about" is used herein to modify a numerical value above and below the stated value by a variance of ±10%.

As used herein, "patient" generally means a mammal (e.g., human) who has been diagnosed with, exhibits symptoms of, or is otherwise believed to be afflicted with a disease, disorder, or condition (such as cancer).

As used herein, "body surface area" (BSA) is calculated using a standard nomogram, e.g., $$BSA\ (m^2) = \sqrt{\frac{Ht\ (cm) \times Wt\ (kg)}{3600}} \text{ or } BSA = \sqrt{\frac{Ht\ (in) \times Wt\ (lb)}{3131}}.$$

The term "combination administration," "administered in combination," and "administering a combination" refers to administering of more than one pharmaceutically active ingredients (including, but not limited to, Compound No. 14 or a pharmaceutically acceptable salt thereof, and a checkpoint inhibitor as disclosed herein) to a patient. Combination administration may refer to simultaneous administration or may refer to sequential administration of Compound No. 14 or a pharmaceutically acceptable salt thereof, and a checkpoint inhibitor as disclosed herein.

The terms "simultaneous" and "simultaneously" refer to the administration of Compound No. 14 or a pharmaceutically acceptable salt thereof, and a checkpoint inhibitor as disclosed herein, to a patient at the same time, or at two different time points that are separated by no more than 2 hours. The simultaneous administration of Compound No. 14 or a pharmaceutically acceptable salt thereof, and a checkpoint inhibitor may be in a single dosage form or in separate dosage forms.

The terms "sequential" and "sequentially" refer to the administration of Compound No. 14 or a pharmaceutically acceptable salt thereof, and a checkpoint inhibitor as disclosed herein, to a patient at two different time points that are separated by more than 2 hours, e.g., about 3 hours, about 4 hours, about 5 hours, about 8 hours, about 12 hours, 1 day, 2 days, 3 days, 4 days, 5 days, 6 days, 7 days or even longer.

The term "intermission" refers to a period that is subsequent to the administration of one or more particular pharmaceutically active ingredients to a patient in an intermittent regimen. Intermission refers to a rest period wherein a particular pharmaceutically active ingredient is not administered for at least one day.

The term "synergistic effect" refers to a situation where the combination of two or more agents produces a greater effect than the sum of the effects of each of the individual agents. The term encompasses not only a reduction in symptoms of the disorder to be treated, but also an improved side effect profile, improved tolerability, improved patient compliance, improved efficacy, or any other improved clinical outcome.

As used herein, the illustrative terms "include", "such as", "for example" and the like (and variations thereof, e.g., "includes" and "including", "examples"), unless otherwise specified, are intended to be non-limiting. That is, unless explicitly stated otherwise, such terms are intended to imply "but not limited to", e.g., "including" means including but not limited to.

Unless otherwise stated, structures depicted herein are meant to include chemical entities which differ only in the presence of one or more isotopically enriched atoms. For example, chemical entities having the present structure except for the replacement of a hydrogen atom by a deuterium or tritium, or the replacement of a carbon atom by a $^{13}$C- or $^{14}$C-enriched carbon are within the scope of the invention.

Unless stereochemical configuration is denoted, structures depicted herein are meant to include all stereochemical forms of the structure, i.e., the R and S configurations for each asymmetric center. Therefore, unless otherwise indicated, single stereochemical isomers as well as enantiomeric, racemic and diastereomeric mixtures of the present chemical entities are within the scope of the invention. When a stereochemical configuration is denoted for a compound, the diastereoisomeric or enantiomeric excess of the compound is at least 99.0%, 99.5%, 99.6%, 99.7%, 99.8% or 99.9%.

STING Agonist

The present disclosure provides a combination treatment for patients with cancer or autoimmune disease. The combination treatment includes, inter alia, administering to a subject in need thereof a therapeutically effective amount of at least one STING agonist.

In some embodiments, the STING agonist is a compound of Formula I, or a pharmaceutically acceptable salt thereof, having the following structure:

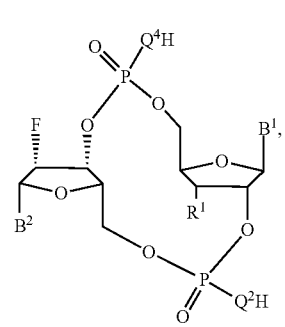

I wherein $R^1$ and $R^2$ are each independently a hydroxy group or a halogen atom;

$B^1$ is:

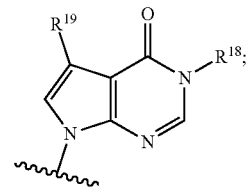

$R^{18}$ is hydrogen or $C_{1-6}$ alkyl;

$R^{19}$ is a halogen atom;

$B^2$ is:

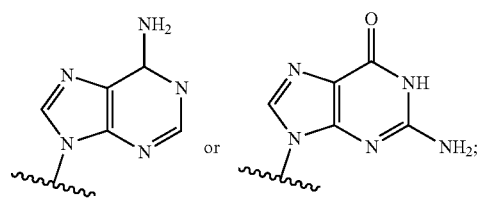 [SMILES: *n1cnc2c1N=CNC2N ; "or" ; *n1cnc2c(=O)[nH]c(N)nc21]

and $Q^2$ and $Q^4$ are each independently an oxygen atom or a sulfur atom.

In some embodiments, the STING agonist is Compound No. 14, or a pharmaceutically acceptable salt thereof, having the following structure:

Compound No. 14

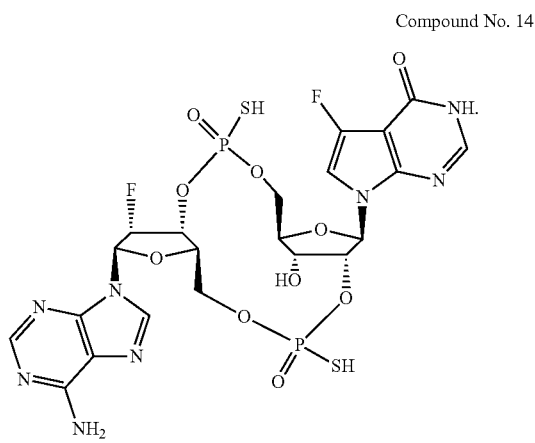 [SMILES: Nc1ncnc2c1ncn2[C@@H]1O[C@@H]2COP(=O)(S)O[C@@H]3[C@H](O)[C@@H](COP(=O)(S)O[C@H]2[C@H]1F)O[C@H]3n1cc(F)c2c(=O)[nH]cnc21]

In some embodiments, the STING agonist is Compound No. 14, or a pharmaceutically acceptable salt thereof.

In some embodiments, the STING agonist is Compound No. 14.

Particular STING agonists, as disclosed herein, are described, for example, in PCT Application Publication No. WO 2018/100558. They may be prepared by methods known to one skilled in the art and/or according to the methods described in WO 2018/100558, which is hereby incorporated by reference in their entirety.

In some embodiments, the STING agonist is Compound No. 14 or a crystalline form thereof.

Checkpoint Inhibitors

The present disclosure provides a combination treatment that includes, inter alia, administering to a subject in need thereof a therapeutically effective amount of at least one checkpoint inhibitor (e.g., nivolumab, pembrolizumab, atezolizumab, durvalumab, avelumab, and ipilimumab). In some embodiments, the checkpoint inhibitor is an anti-PD-1 antibody. In some embodiments, the checkpoint inhibitor is an anti-PD-L1 antibody. In some embodiments, the checkpoint inhibitor is an anti-CTLA-4 antibody.

PD-1 is a type I transmembrane protein that is one of the major immune checkpoint molecules (Blank et al., 2005, Cancer Immunotherapy, 54:307-314). PD-1 is primarily expressed on activated T cells, and it interacts with the ligands PD-L1 (B7-H1 or CD274) and PD-L2 (B7-DC or CD273) to induce an inhibitory signal resulting in reduced T cell proliferation, cytokine production, and cytotoxic activity (Freeman et al., 2000, J. Exp. Med., 192:1027-34).

In some embodiments, the anti-PD-1 antibody is a fully human monoclonal antibody. In some embodiments, the anti-PD-1 antibody is a humanized IgG monoclonal antibody.

In some embodiments, the anti-PD-1 antibody is a full length (intact) antibody. In some embodiments, the anti-PD-1 antibody consists of anti-PD-1 binding fragments, including, but not limited to, Fab, Fab', F(ab')$_2$, and Fv fragments, single chain Fv fragments, and single chain domain fragments.

In some embodiments, the anti-PD-1 antibody is a derivatized antibody. In some embodiments, the anti-PD-1 antibody is derivatized by glycosylation, acetylation, pegylation, phosphorylation, and amidation. In some embodiments, the anti-PD-1 antibody is derivatized by known protecting/blocking groups, proteolytic cleavage, linkage to a cellular ligand or other protein. In some embodiments, the derivatized anti-PD-1 antibody can contain one or more non-natural amino acids, e.g., using ambrx technology (See, e.g., Wolfson, 2006, Chem. Biol. 13(10):1011-2).

In some embodiments, the anti-PD-1 antibody is nivolumab.

Nivolumab is a human monoclonal antibody that blocks the interaction between PD-1 and its ligands, PD-L1 and PD-L2. Nivolumab is an IgG4 kappa immunoglobulin that has a calculated molecular mass of 146 kDa. It is expressed in a recombinant Chinese Hamster Ovary (CHO) cell line. Nivolumab is approved by the FDA for treating unresectable or metastatic melanoma, melanoma, metastatic non-small cell lung cancer, advanced renal cell carcinoma, classical Hodgkin lymphoma, squamous cell carcinoma of the head and neck, urothelial carcinoma, microsatellite instability-high (MSI-H) or mismatch repair deficient (dMMR) metastatic colorectal cancer, and hepatocellular carcinoma. Nivolumab is commercially available as Opdivo®.

In some embodiments, the anti-PD-1 antibody is pembrolizumab.

Pembrolizumab is a humanized monoclonal antibody that blocks the interaction between PD-1 and its ligands, PD-L1 and PD-L2. Pembrolizumab is an IgG4 kappa immunoglobulin with an approximate molecular mass of 149 kDa. Pembrolizumab is produced in recombinant Chinese hamster ovary (CHO) cells. Pembrolizumab is approved by the FDA for treating melanoma, non-small cell lung cancer, head and neck cancer, classical Hodgkin lymphoma, primary mediastinal large B-cell lymphoma, urothelial carcinoma, microsatellite instability-high cancer, gastric cancer, and cervical cancer. Pembrolizumab is commercially available as Keytruda®.

In some embodiments, the anti-PD-1 antibody is cemiplimab.

Cemiplimab is a human monoclonal antibody that binds to PD-1 and blocks its interaction with PD-L1 and PD-L2. Cemiplimab is an IgG4 immunoglobulin with an approximate molecular mass of 146 kDa. Cemiplimab is produced by recombinant DNA technology in Chinese hamster ovary (CHO) cell suspension. Cemiplimab is approved by the FDA for treating metastatic cutaneous squamous cell carcinoma (CSCC) or locally advanced CSCC who are not candidates for curative surgery or curative radiation. Cemiplimab is commercially available as Libtayo®.

Additional anti-PD-1 antibodies include, for example, pidilizumab (Medivation), BMS-936559 (Bristol-Myers Squibb), and AMP-224.

In some embodiments, the anti-PD-1 antibody used in the methods (and kits) described herein is nivolumab or an anti-PD-1 antibody that binds to the same epitope as nivolumab. In some embodiments, the anti-PD-1 antibody is nivolumab.

In some embodiments, the anti-PD-1 antibody used in the methods (and kits) described herein is pembrolizumab or an anti-PD-1 antibody that binds to the same epitope as pembrolizumab. In some embodiments, the anti-PD-1 antibody is pembrolizumab.

PD-L1 is a type I transmembrane protein that comprises an extracellular Ig-V like domain, an Ig-C like domain, a transmembrane domain and an intracellular C-terminus domain. PD-L1 is expressed in a broad range of cancers with a high frequency, including tumor cells and/or tumor infiltrating immune cells and can contribute to the inhibition of the anti-tumor immune response in the tumor microenvironment. In some cancers, expression of PD-L1 has been associated with reduced survival and unfavorable prognosis. PD-L1 is expressed on many cell types, including T-cells, B-cells, endothelial, epithelial, and antigen presenting cells, on cells of lung, liver and heart tissues, and on several types of tumor cells. Expression of PD-L1 on the cell surface has also been shown to be upregulated through IFN-γ stimulation. There are at least 4 variants of PD-1 that have been cloned from activated human T cells, including transcripts lacking (i) exon 2, (ii) exon 3. (iii) exons 2 and 3 or (iv) exons 2 through 4. Nielsen et al., Cell. Immunol. 235: 109-16 (2005). The amino acid sequence of a human PD-L1 is represented in GenBank Accession No. NP 054862.1.

In some embodiments, the anti-PD-L1 antibody is a full length (intact) antibody. In some embodiments, the anti-PD-L1 antibody consists of anti-PD-L1 binding fragments, including, but not limited to, Fab, F(ab')$_2$, Fd, Fv, and dAb fragments, single chain Fv fragments, and PD-L1-binding domain immunoglobulin fusion proteins.

In some embodiments, the anti-PD-L1 antibody is atezolizumab.

Atezolizumab is a programmed cell death ligand 1 (PD-L1) blocking antibody. Atezolizumab is an Fc-engineered, humanized, non-glycosylated IgG1 kappa immunoglobulin that has a calculated molecular mass of 145 kDa. Atezolizumab is approved by the FDA for treating locally advanced or metastatic urothelial carcinoma and metastatic non-small cell lung cancer. Atezolizumab is commercially available as Tecentriq®.

In some embodiments, the anti-PD-L1 antibody is durvalumab.

Durvalumab is a programmed cell death ligand 1 (PD-L1) blocking antibody. Durvalumab is a human immunoglobulin G1 kappa (IgG1$_\kappa$) monoclonal antibody that is produced by recombinant DNA technology in Chinese Hamster Ovary (CHO) cell suspension culture. Durvalumab is approved by the FDA for treating urothelial carcinoma and non-small cell lung cancer. Durvalumab is commercially available as Imfinzi®.

In some embodiments, the anti-PD-L1 antibody is avelumab.

Avelumab is a programmed death ligand-1 (PD-L1) blocking antibody. Avelumab is a human IgG1 lambda monoclonal antibody that has a molecular weight of approximately 147 kDa. Avelumab is approved by the FDA for treating metastatic Merkel cell carcinoma and locally advanced or metastatic urothelial carcinoma. Avelumab is commercially available as Bavencio®.

Additional anti-PD-L1 antibodies include, for example, YW243.55.S70 (U.S. Pat. No. 8,217,149), MEDI-4736, MSB-0010718C, LY3300054 (Eli Lilly and Co.), BMS-936559 (Bristol-Meyers Squibb), MPDL3280A, and MDX-1105.

In some embodiments, the anti-PD-L1 antibody used in the methods (and kits) described herein is atezolizumab or an anti-PD-L1 antibody that binds to the same epitope as atezolizumab. In some embodiments, the anti-PD-L1 antibody is atezolizumab.

In some embodiments, the anti-PD-L1 antibody used in the methods (and kits) described herein is durvalumab or an anti-PD-L1 antibody that binds to the same epitope as durvalumab. In some embodiments, the anti-PD-L1 antibody is durvalumab.

In some embodiments, the anti-PD-L1 antibody used in the methods (and kits) described herein is avelumab or an anti-PD-L1 antibody that binds to the same epitope as avelumab. In some embodiments, the anti-PD-L1 antibody is avelumab.

CTLA-4 is a Type I transmembrane protein encoded in humans by the CTLA-4 gene. CTLA-4 has been found to have a correlation with cancer growth and development due to its negative role in immune response. CTLA-4 is expressed at the cell surface of activated CD4+ and CD8+ T cells, and is an important negative regulator of T cells function. CTLA-4 has been shown to negatively regulate immune activation through both intrinsic and extrinsic mechanisms (Grosso and Kunkel, Cancer Immunity (2013) 13: 5). Inhibition of negative regulation by CTLA-4 has been shown to promote stimulation of adaptive immune response and T cell activation. A representative amino acid sequence of human CTLA-4 can be found under GenBank accession number: AAL07473.1, and a representative mRNA nucleic acid sequence encoding human CTLA-4 can be found under GenBank accession number: AF414120.1.

In some embodiments, the anti-CTLA-4 antibody is a full length (intact) antibody. In some embodiments, the anti-CTLA-4 antibody consists of anti-CTLA-4 binding fragments, including, but not limited to, Fab, Fab', F(ab')$_2$, Fv, and single chain fragments, a diabody, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody, a camelized single domain antibody, a nanobody, a domain antibody, and a bivalent domain antibody.

In some embodiments, the anti-CTLA-4 antibody is ipilimumab.

Ipilimumab is a recombinant, human monoclonal antibody that binds to the cytotoxic T-lymphocyte-associated antigen 4 (CTLA-4). Ipilimumab is an IgG1 kappa immunoglobulin with an approximate molecular mass of 148 kDa. Ipilimumab is produced in mammalian (Chinese hamster ovary) cell culture. Ipilimumab is approved by the FDA for treating unresectable or metastatic melanoma, adjuvant treatment of melanoma, and advanced renal cell carcinoma. Ipilimumab is commercially available as Yervoy®.

Additional anti-CTLA-4 antibodies include, for example, tremelimumab.

In some embodiments, the anti-CTLA-4 antibody used in the methods (and kits) described herein is ipilimumab or an anti-CTLA-4 antibody that binds to the same epitope as ipilimumab. In some embodiments, the anti-CTLA-4 antibody is ipilimumab.

Methods of Treating Cancer

In some embodiments, the present disclosure relates to a method of treating cancer in a patient by administering to a patient in need of said treating a combination of a STING agonist or pharmaceutically acceptable salt thereof and one or more checkpoint inhibitors.

In some embodiments, the present disclosure relates to a method of treating cancer by administering to a patient in need of said treating a combination of a STING agonist and a checkpoint inhibitor.

In some embodiments, the present disclosure relates to the use of a STING agonist in combination with a checkpoint inhibitor for the treatment of cancer in a patient.

In some embodiments, the present disclosure relates to a composition comprising a STING agonist for use in treating cancer in a patient, wherein the patient is also treated with a checkpoint inhibitor. In some aspects, the disclosure relates to a composition comprising a STING agonist for use in treating cancer in a patient, wherein the STING agonist is in combination with the checkpoint inhibitor. In some embodiments, the STING agonist can be administered simultaneously or sequentially with the checkpoint inhibitor.

In some embodiments, the present disclosure relates to methods of treating cancer comprising administering to a patient in need of such treatment, a therapeutically effective amount of a combination of a STING agonist and a checkpoint inhibitor.

In some embodiments, the present disclosure relates to a method of treating cancer by administering to a patient a combination of Compound No. 14, or pharmaceutically acceptable salt thereof, and a checkpoint inhibitor.

In another aspect, the present disclosure relates to the use of Compound No. 14, or a pharmaceutically acceptable salt thereof, in combination with a checkpoint inhibitor for the treatment of cancer.

In some embodiments, the methods of treating cancer, as described herein, can include a combination of a STING agonist, a checkpoint inhibitor, and one or more additional therapeutic agents. In some embodiments, the one or more additional therapeutic agents can be chemotherapeutic agents. In some embodiments, the one or more additional therapeutic agents can include, but are not limited to, fludarabine, cyclophosphamide, doxorubicin, vincristine, methotrexate anthracycline-based chemotherapeutic agents, prednisone, methylprednisolone, glucocorticoids, Ibritumomab tiuxetan, acetaminophen, antihistamines, and combinations thereof. In another embodiment, the checkpoint inhibitor is coadministered with human hyaluronidase.

In some embodiments, the present disclosure relates to a method of treating a disorder, wherein the disorder is cancer.

In some embodiments, the cancer is a solid tumor. In some embodiments, the cancer is a metastatic solid tumor. In some embodiments, the cancer is an advanced solid tumor. Non-limiting examples of solid tumors include pancreatic cancer; bladder cancer, including invasive bladder cancer; colorectal cancer, including microsatellite instability-high (MSI-H) or mismatch repair deficient (dMMR) metastatic colorectal cancer; thyroid cancer; gastric cancer; breast cancer, including metastatic breast cancer; prostate cancer, including androgen-dependent and androgen-independent prostate cancer; renal cancer, including, e.g., metastatic renal cell carcinoma and advanced renal cell carcinoma; urothelial carcinoma, including locally advanced or metastatic urothelial carcinoma; microsatellite instability-high cancer; liver cancer including e.g. hepatocellular carcinoma and intrahepatic bile duct cancer; lung and bronchus cancer including non-small cell lung cancer (NSCLC), squamous lung cancer, brochioloalveolar carcinoma (BAC), adenocarcinoma of the lung, and small cell lung cancer (SCLC); ovarian cancer including, e.g., progressive epithelial and primary peritoneal cancer; cervical cancer; uterine cancer including e.g. uterine corpus and uterine cervix; endometrial cancer; esophageal cancer; head and neck cancer, including, e.g., squamous cell carcinoma of the head and neck, nasopharyngeal caner, oral cavity and pharynx; melanoma, including unresectable or metastatic melanoma, and adjuvant treatment of melanoma; metastatic Merkel cell carcinoma; neuroendocrine cancer, including metastatic neuroendocrine tumors; brain cancer, including, e.g., glioma/glioblastoma, anaplastic oligodendroglioma, adult glioblastoma multiforme, and adult anaplastic astrocytoma; neuroendocrine cancer, including metastatic neuroendocrine tumors; bone cancer; gastroesophageal junction cancer, and soft tissue sarcoma.

In some embodiments, the cancer is a hematological cancer. Non-limiting examples of hematologic malignancies include acute myeloid leukemia (AML); chronic myelogenous leukemia (CML), including accelerated CIVIL and CML blast phase (CML-BP); acute lymphoblastic leukemia (ALL); chronic lymphocytic leukemia (CLL); Hodgkin's lymphoma (HL), including classical Hodgkin lymphoma; non-Hodgkin's lymphoma (NHL), including B-cell lymphoma, T-cell lymphoma, follicular lymphoma (FL), marginal zone lymphoma (MZL), mantle cell lymphoma (MCL), diffuse large B-cell lymphoma (DLBCL), primary mediastinal large B-cell lymphoma, and Burkitt lymphoma; multiple myeloma (MM); amyloidosis; Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes. In some embodiments, the cancer is chronic lymphocytic leukemia (CLL), Hodgkin's lymphoma, or non-Hodgkin's lymphoma including follicular lymphoma (FL), marginal zone lymphoma (MZL), mantle cell lymphoma (MCL), Diffuse large B-cell lymphoma (DLBCL) and Burkitt lymphoma.

In some embodiments, the cancer is melanoma, lung cancer, renal cancer, lymphoma, head and neck cancer, urothelial cancer, prostate cancer, bladder cancer, breast cancer, gastric cancer, colorectal cancer, leukemia, cervical cancer, microsatellite instability-high cancer, hepatocellular carcinoma, or Merkel cell carcinoma.

In some embodiments, the melanoma is metastatic melanoma, unresectable melanoma, or cutaneous melanoma.

In some embodiments, the lung cancer is non-small cell lung cancer or small cell lung cancer.

In some embodiments, the non-small cell lung cancer is metastatic non-small cell lung cancer, metastatic squamous non-small cell lung cancer, or metastatic nonsquamous non-small cell lung cancer.

In some embodiments, the renal cancer is renal cell carcinoma.

In some embodiments, the lymphoma is classical Hodgkin lymphoma or primary mediastinal large B-cell lymphoma.

In some embodiments, the head and neck cancer is head and neck squamous cell carcinoma.

In some embodiments, the urothelial cancer is urothelial carcinoma.

In some embodiments, the prostate cancer is hormone-refractory prostate cancer.

In some embodiments, the gastric cancer is gastroesophageal junction adenocarcinoma.

In some embodiments, the cancer is microsatellite instability-high cancer.

In some embodiments, the cancer is relapsed. In some embodiments, relapsed cancer is cancer which has returned after a period of time in which no cancer could be detected.

In some embodiments, the cancer is refractory. In some embodiments, refractory cancer does not respond to cancer treatment; it is also known as resistant cancer. In some embodiments, the cancer is resistant to rituximab. In some embodiments, the cancer does not respond to the treatment of rituximab. In some embodiments, the cancer is rituximab-resistant recurrent cancer. In some embodiments, the patient has become refractory to a rituximab-containing regimen. In some embodiments, the tumor is unresectable. In some embodiments, an unresectable tumor is unable to be removed by surgery. In some embodiments, the cancer has not been previously treated. In some embodiments, the cancer is locally advanced. In some embodiments, "locally advanced" refers to cancer that is somewhat extensive but still confined to one area. In some instances, "locally advanced" may refer to a small tumor that hasn't spread but has invaded nearby organs or tissues that make it difficult to remove with surgery alone. In some embodiments, the cancer is metastatic. In some embodiments, metastatic cancer is a cancer that has spread from the part of the body where it started (the primary site) to other parts of the body.

In some embodiments, the present disclosure relates to a method of treating a disorder, wherein the disorder is an autoimmune disease.

In some embodiments, the disorder is a STING-mediated disorder.

In some embodiments, the disorder is a PD-1-positive cancer. A PD-1-positive cancer includes a cancer where PD-1 is expressed on the cancer cells.

In some embodiments, the disorder is a PD-L1-positive cancer. A PD-L1-positive cancer includes a cancer where PD-L1 is expressed on the cancer cells.

In some embodiments, the disorder is a CTLA-4-positive cancer. A CTLA-4-positive cancer includes a cancer where CTLA-4 is expressed on the cancer cells.

Medicament

In some embodiments, the present disclosure relates to a medicament for use in treating cancer in a patient in need of such treatment. The medicament comprises a STING agonist and a checkpoint inhibitor, and is in single dosage form or in separate dosage forms.

In some embodiments, the medicaments, as described herein, can include a combination of a STING agonist, a checkpoint inhibitor, and optionally one or more additional therapeutic agents.

In some embodiments, the present disclosure relates to the use of a STING agonist in the manufacture of a medicament for treating cancer, wherein the STING agonist is administered with a checkpoint inhibitor, and wherein the medicament is in single dosage form or in separate dosage forms. In some embodiments, the STING agonist is administered with a checkpoint inhibitor and one or more additional therapeutic agents.

In some embodiments, the present disclosure relates to the use of a STING agonist for the manufacture of a medicament in treating cancer in a patient, wherein the patient is also treated with a checkpoint inhibitor, and optionally one or more additional therapeutic agents. In some embodiments, the STING agonist may be administered simultaneously or sequentially with the checkpoint inhibitor. In some aspects, the present disclosure relates to the use of a STING agonist for the manufacture of a medicament in treating cancer in a patient, wherein the STING agonist is in combination with a checkpoint inhibitor, and optionally one or more additional therapeutic agents. In some embodiments, the STING agonist is in the same composition as the checkpoint inhibitor. In some embodiments, the STING agonist is in a separate composition as the checkpoint inhibitor. In some embodiments, the STING agonist is in the same composition as one or more additional therapeutic agents. In some embodiments, the STING agonist is in the same composition as the checkpoint inhibitor, and optionally one or more additional therapeutic agents. In some embodiments, the STING agonist is in a separate composition as one or more additional therapeutic agents. In some embodiments, the STING agonist is in a separate composition as the checkpoint inhibitor, and optionally one or more additional therapeutic agents.

In another aspect, the present disclosure relates to the use of Compound No. 14, or a pharmaceutically acceptable salt thereof in combination with a checkpoint inhibitor in the manufacture of a medicament for use in treating cancer. In some embodiments, the present disclosure relates to the use of Compound No. 14, or a pharmaceutically acceptable salt thereof in combination with a checkpoint inhibitor, and optionally one or more additional therapeutic agents in the manufacture of a medicament for use in treating cancer.

In another aspect, the present disclosure relates to the use of Compound No. 14, or a pharmaceutically acceptable salt thereof, in the manufacture of a medicament for treating cancer, wherein Compound No. 14 or a pharmaceutically acceptable salt thereof is administered with a checkpoint inhibitor, and optionally one or more additional therapeutic agents.

In some embodiments, the one or more additional therapeutic agents can be chemotherapeutic agents. In some embodiments, the one or more additional therapeutic agents can include, but are not limited to, fludarabine, cyclophosphamide, doxorubicin, vincristine, methotrexate anthracycline-based chemotherapeutic agents, prednisone, methylprednisolone, glucocorticoids, Ibritumomab tiuxetan, acetaminophen, antihistamines, and combinations thereof. In another embodiment, the checkpoint inhibitor is coadministered with human hyaluronidase.

Administration of the Combination

Compound No. 14 or a pharmaceutically acceptable salt thereof, may be administered in combination with the checkpoint inhibitor, and optionally one or more additional therapeutic agents, in a single dosage form or as a separate dosage forms. In some embodiments, when administered as a separate dosage form, the checkpoint inhibitor may be administered prior to, at the same time as, or following administration of Compound No. 14 or a pharmaceutically acceptable salt thereof. In some embodiments, when administered as a separate dosage form, one or more doses of Compound No. 14 or a pharmaceutically acceptable salt thereof, may be administered prior to the checkpoint inhibitor. In some embodiments, the checkpoint inhibitor is administered prior to the administration of Compound No. 14 or a pharmaceutically acceptable salt thereof. As used herein, the administration in "combination" of Compound No. 14 or a pharmaceutically acceptable salt thereof, a checkpoint inhibitor, and optionally one or more additional therapeutic agents refers not only to simultaneous or sequential administration of the agents, but also to the administration of the agents during a single treatment cycle, as understood by one skilled in the art. When Compound No. 14 or a pharmaceutically acceptable salt thereof is administered in combination with the checkpoint inhibitor, and optionally one or more additional therapeutic agents, a therapeutically effective amount of the combination is administered.

The STING agonist may be administered by any method known to one skilled in the art. For example, in some embodiments, the STING agonist may be administered in the form of a pharmaceutical composition of the STING agonist and a pharmaceutically acceptable carrier, such as those described herein. In some embodiments, the pharmaceutical composition is suitable for oral administration. In some embodiments, the pharmaceutical composition is a tablet or a capsule that is suitable for oral administration. In some other embodiments, the pharmaceutical composition is a liquid dosage form suitable for oral administration. In some embodiments, the pharmaceutical composition is suitable for parenteral administration. In some embodiments, the pharmaceutical composition is suitable for intravenous administration. In some embodiments, the pharmaceutical composition is suitable for intravenous infusion. In some embodiments, the pharmaceutical composition is suitable for injection. In some embodiments, the pharmaceutical composition is suitable for intravenous injection. In some embodiments, the pharmaceutical composition is suitable for subcutaneous injection. In some embodiments, these compositions optionally further comprise one or more additional therapeutic agents.

The checkpoint inhibitor may be administered by any method known to one skilled in the art. In some embodiments, the checkpoint inhibitor is administered intravenously (i.v.). In some embodiments, the checkpoint inhibitor is administered subcutaneously (s.c.). In some embodiments, the checkpoint inhibitor is administered orally. For example, the checkpoint inhibitor may be administered in the form of a second composition, in some embodiments, a pharmaceutical composition of the checkpoint inhibitor and a pharmaceutically acceptable carrier, such as those described herein. In some aspects, the pharmaceutical composition is suitable for oral administration. In some embodiments, the pharmaceutical composition is a tablet or a capsule that is suitable for oral administration. In some other embodiments, the pharmaceutical composition is a liquid dosage form suitable for oral administration. In some embodiments, these compositions optionally further comprise one or more additional therapeutic agents.

In some embodiments, the checkpoint inhibitor may be administered orally, parenterally, by inhalation spray, topically, rectally, nasally, buccally, vaginally or via an implanted reservoir. The term "parenteral" as used herein includes subcutaneous, intravenous, intraperitoneal, intramuscular, intra-articular, intra-synovial, intrasternal, intrathecal, intrahepatic, intralesional and intracranial injection or infusion techniques. In some embodiments, the checkpoint inhibitor is administered orally, intravenously or subcutaneously. In some embodiments, the checkpoint inhibitor is administered orally. In some embodiments, the checkpoint inhibitor is administered intravenously. In some embodiments, the intravenous administration can be intravenous infusion or intravenous injection. In some embodiments, the checkpoint inhibitor is administered by an intravenous infusion. In some embodiments, the checkpoint inhibitor is administered by an intravenous injection. In some embodiments, the checkpoint inhibitor is administered by subcutaneous injection. In some embodiments, the checkpoint inhibitor is administered by intravenous infusion and then subsequently administered by subcutaneous injection. In another embodiment, the checkpoint inhibitor is coadministered with human hyaluronidase subcutaneously. These methods of administration may be designed to be short-acting, fast-releasing, or long-acting. Furthermore, the checkpoint inhibitor may be administered in a local rather than systemic means, such as administration (e.g., by injection) at a tumor site.

In some embodiments, the checkpoint inhibitor may also be administered by nasal aerosol or inhalation. The checkpoint inhibitor may be prepared according to techniques well known in the art and may be prepared as solutions in saline, employing benzyl alcohol or other suitable preservatives, absorption promoters to enhance bioavailability, fluorocarbons, and/or other conventional solubilizing or dispersing agents.

The amounts or suitable doses of the methods of this disclosure depends upon a number of factors, including the nature of the severity of the condition to be treated, the particular inhibitor, the route of administration and the age, weight, general health, and response of the individual patient. In some embodiments, the suitable dose level is one that achieves a therapeutic response as measured by tumor regression, or other standard measures of disease progression, progression free survival or overall survival. In some embodiments, the suitable dose level is one that achieves this therapeutic response and also minimizes any side effects associated with the administration of the therapeutic agent. The suitable dose levels may be ones that prolong the therapeutic response and/or prolong life.

It will be understood that a suitable dose of the STING agonist, the checkpoint inhibitor, and optionally one or more additional therapeutic agents may be taken at any time of the day or night. In some embodiments, a suitable dose of each agent is taken in the morning. In some other embodiments, a suitable dose of each agent is taken in the evening. In some embodiments, a suitable dose of each of the agents is taken both in the morning and the evening. It will be understood that a suitable dose of each agent may be taken with or without food. In some embodiments a suitable dose of an agent is taken with a meal. In some embodiments a suitable dose of an agent is taken while fasting.

In some embodiments, Compound No. 14 or a pharmaceutically acceptable salt thereof is administered on a daily schedule. In some embodiments, Compound No. 14 or a pharmaceutically acceptable salt thereof is administered every other day. In some embodiments, Compound No. 14 or a pharmaceutically acceptable salt thereof is administered once every three days. In some embodiments, Compound No. 14 or a pharmaceutically acceptable salt thereof is administered once every three days for three doses. In some embodiments, Compound No. 14 or a pharmaceutically acceptable salt thereof is administered on a twice-weekly schedule. In some embodiments, Compound No. 14 or a pharmaceutically acceptable salt thereof is administered on a three times a week schedule. In some embodiments, Compound No. 14 or a pharmaceutically acceptable salt thereof is administered on a weekly schedule. In some embodiments, Compound No. 14 or a pharmaceutically acceptable salt thereof is administered on a once every two weeks schedule.

In some embodiments, Compound No. 14 or a pharmaceutically acceptable salt thereof is administered once per day. In some embodiments, Compound No. 14 or a pharmaceutically acceptable salt thereof is administered twice per day. In some embodiments, Compound No. 14 or a pharmaceutically acceptable salt thereof is administered three times per day.

In some embodiments, Compound No. 14 or a pharmaceutically acceptable salt thereof is administered at least 3 times on alternate days within a 7-day cycle. In some embodiments, Compound No. 14 or a pharmaceutically acceptable salt thereof is administered on day 1 and day 4 of a 7-day cycle. In some embodiments, Compound No. 14 or a pharmaceutically acceptable salt thereof is administered on consecutive days in a 7-day cycle followed by an intermission. In some embodiments, Compound No. 14 or a pharmaceutically acceptable salt thereof is administered for 2 consecutive days followed by an intermission of 5 consecutive days for at least one 7-day cycle. In some embodiments, Compound No. 14 or a pharmaceutically acceptable salt thereof is administered for 3 consecutive days followed by an intermission of 4 consecutive days for at least one 7-day cycle. In some embodiments, Compound No. 14 or a pharmaceutically acceptable salt thereof is administered for 4 consecutive days followed by an intermission of 3 consecutive days for at least one 7-day cycle. In some embodiments, Compound No. 14 or a pharmaceutically acceptable salt thereof is administered for 5 consecutive days followed by an intermission of 2 consecutive days for at least one 7-day cycle. In some embodiments, there will be periods of rest between one or more of the 7-day treatment cycles. In some embodiments, there will be a 7-day rest between one or more of the 7-day treatment cycles.

The present description contemplates administration of the STING agonist for one or more treatment cycles, for example, 1, 2, 3, 4, 5, 6, or more, treatment cycles. In some embodiments, a treatment cycle is about 7 days to about 56 days, or more. In some embodiments, a treatment cycle is 7 days, 14 days, 21 days, 28 days, 35 days, 42 days, 49 days, or 56 days. In some embodiments, a treatment cycle is 21 days or 28 days. In some embodiments, there will be periods of rest within or between one or more of the treatment cycles. For example, in some embodiments, there will be a period of rest at the end of the treatment cycle. In some embodiments, there will be a period of rest between the second and third treatment cycle but not the first and second treatment cycle. In another embodiment, there might be a period of rest between the first and second treatment cycle but not the second and third treatment cycle. Dosing schedules include, for example, administering the STING agonist once during a treatment schedule, e.g., on day 1 of a 21 day cycle, twice during a treatment cycle, e.g., on days 1 and 15 of a 21 day cycle or on days 1 and 15 of a 28 day cycle, three times during a treatment cycle, e.g., on days 1, 8 and 15 of a 21 day cycle or on days 1, 8 and 15 of a 28 day cycle, and four times during a treatment cycle, e.g., on days 1, 4, 8, and 11 of a 21 day cycle or of on days 1, 4, 8, and 11 of a 28 day cycle. Other dosage schedules are encompassed by the present invention.

In some embodiments, Compound No. 14 or a pharmaceutically acceptable salt thereof is administered within a 21-day cycle. In some embodiments, Compound No. 14 or a pharmaceutically acceptable salt thereof is administered at least four times within a 21-day cycle. In some embodiments, Compound No. 14 or a pharmaceutically acceptable salt thereof is administered on day 1 within a 21-day cycle. In some embodiments, Compound No. 14 or a pharmaceutically acceptable salt thereof is administered on day 4 within a 21-day cycle. In some embodiments, Compound No. 14 or a pharmaceutically acceptable salt thereof is administered on day 8 within a 21-day cycle. In some embodiments, Compound No. 14 or a pharmaceutically acceptable salt thereof is administered on day 11 within a 21-day cycle. In some embodiments, Compound No. 14 or a pharmaceutically acceptable salt thereof is administered on days 1, 4, 8, and 11 within a 21-day cycle.

In some embodiments, Compound No. 14 or a pharmaceutically acceptable salt thereof is administered within a 21-day cycle. In some embodiments, Compound No. 14 or a pharmaceutically acceptable salt thereof is administered at least two times within a 21-day cycle. In some embodiments, Compound No. 14 or a pharmaceutically acceptable salt thereof is administered on day 1 within a 21-day cycle. In some embodiments, Compound No. 14 or a pharmaceutically acceptable salt thereof is administered on day 8 within a 21-day cycle. In some embodiments, Compound No. 14 or a pharmaceutically acceptable salt thereof is administered on days 1 and 8 within a 21-day cycle.

In some embodiments, Compound No. 14 or a pharmaceutically acceptable salt thereof is administered for a duration of 1 year or less. In some embodiments, Compound No. 14 or a pharmaceutically acceptable salt thereof is administered for a duration of 1 year or more.

In some embodiments, the amount of Compound No. 14 or a pharmaceutically acceptable salt thereof that is administered on each day of dosing is about 0.5 mg to about 1000 mg. In some embodiments, the amount of Compound No. 14 or a pharmaceutically acceptable salt thereof that is administered on each day of dosing is about 0.5 mg to about 300 mg. In some embodiments, the amount of Compound No. 14 or a pharmaceutically acceptable salt thereof that is administered on each day of dosing is about 1 mg to about 300 mg. In some embodiments, the amount of Compound No. 14 or a pharmaceutically acceptable salt thereof that is administered on each day of dosing is about 3 mg to about 300 mg. In some embodiments, the amount of Compound No. 14 or a pharmaceutically acceptable salt thereof that is administered on each day of dosing is about 0.5 mg to about 200 mg. In some embodiments, the amount of Compound No. 14 or a pharmaceutically acceptable salt thereof that is administered on each day of dosing is about 1 mg to about 200 mg. In some embodiments, the amount of Compound No. 14 or a pharmaceutically acceptable salt thereof that is administered on each day of dosing is about 10 mg to about 200 mg. In some embodiments, the amount of Compound No. 14 or a pharmaceutically acceptable salt thereof that is administered on each day of dosing is about 0.5 mg to about 100 mg. In some embodiments, the amount of Compound No. 14 or a pharmaceutically acceptable salt thereof that is administered on each day of dosing is about 0.5 mg to about 50 mg. In some embodiments, the amount of Compound No. 14 or a pharmaceutically acceptable salt thereof that is administered on each day of dosing is about 0.5 mg to about 10 mg. In some embodiments, the amount of Compound No. 14 or a pharmaceutically acceptable salt thereof that is administered on each day of dosing is about 0.5 mg to about 5 mg. In some embodiments, the amount of Compound No. 14 or a pharmaceutically acceptable salt thereof that is administered on each day of dosing is about 1 mg to about 3 mg. In some embodiments, the amount of Compound No. 14 or a pharmaceutically acceptable salt thereof that is administered on each day of dosing is about 2 mg to about 5 mg. In some embodiments, the amount of Compound No. 14 or a pharmaceutically acceptable salt thereof that is administered on each day of dosing is about 5 mg to about 10 mg. In some embodiments, the amount of Compound No. 14 or a pharmaceutically acceptable salt thereof that is administered on each day of dosing is about 5 mg to about 15 mg. In some embodiments, the amount of Compound No. 14 or a pharmaceutically acceptable salt thereof that is administered on each day of dosing is about 10 mg to about 20 mg. In some embodiments, the amount of Compound No. 14 or a pharmaceutically acceptable salt thereof that is administered on each day of dosing is about 15 mg to about 25 mg. In some embodiments, the amount of Compound No. 14 or a pharmaceutically acceptable salt thereof that is administered on each day of dosing is between about 20 mg to about 30 mg. In some embodiments, the amount of Compound No. 14 or a pharmaceutically acceptable salt thereof that is administered on each day of dosing is between about 25 mg to about 35 mg. In some embodiments, the amount of Compound No. 14 or a pharmaceutically acceptable salt thereof that is administered on each day of dosing is between about 30 mg to about 40 mg. In some embodiments, the amount of Compound No. 14 or a pharmaceutically acceptable salt thereof that is administered on each day of dosing is between about 35 mg to about 45 mg. In some embodiments, the amount of Compound No. 14 or a pharmaceutically acceptable salt thereof that is administered on each day of dosing is between about 40 mg to about 50 mg. In some embodiments, the amount of Compound No. 14 or a pharmaceutically acceptable salt thereof that is administered on each day of dosing is between about 55 mg to about 65 mg. In some embodiments, the amount of Compound No. 14 or a pharmaceutically acceptable salt thereof that is administered on each day of dosing is between about 50 mg to about 100 mg. In some embodiments, the amount of Compound No. 14 or a pharmaceutically acceptable salt thereof that is administered on each day of dosing is between about 90 mg to about 150 mg. In some embodiments, the amount of Compound No. 14 or a pharmaceutically acceptable salt thereof that is administered on each day of dosing is between about 140 mg to about 200 mg. In some embodiments, the amount of Compound No. 14 or a pharmaceutically acceptable salt thereof that is administered on each day of dosing is between about 190 mg to about 250 mg. In some embodiments, the amount of Compound No. 14 or a pharmaceutically acceptable salt thereof that is administered on each day of dosing is between about 240 mg to about 300 mg. In some embodiments, the amount of Compound No. 14 or a pharmaceutically acceptable salt thereof that is administered on each day of dosing is between about 290 mg to about 350 mg. In some embodiments, the amount of Compound No. 14 or a pharmaceutically acceptable salt thereof that is administered on each day of dosing is between about 340 mg to about 400 mg. In some embodiments, the amount of Compound No. 14 or a pharmaceutically acceptable salt thereof that is administered on each day of dosing is between about 390 mg to about 450 mg. In some embodiments, the amount of Compound No. 14 or a pharmaceutically acceptable salt thereof that is administered on each day of dosing is between about 440 mg to about 500 mg.

In some embodiments, the amount of Compound No. 14 or a pharmaceutically acceptable salt thereof that is administered on each day of dosing is about 0.5 mg. In some embodiments, the amount of Compound No. 14 or a pharmaceutically acceptable salt thereof that is administered on each day of dosing is about 1 mg. In some embodiments, the amount of Compound No. 14 or a pharmaceutically acceptable salt thereof that is administered on each day of dosing is about 2 mg. In some embodiments, the amount of Compound No. 14 or a pharmaceutically acceptable salt thereof that is administered on each day of dosing is about 3 mg. In some embodiments, the amount of Compound No. 14 or a pharmaceutically acceptable salt thereof that is administered on each day of dosing is about 4 mg. In some embodiments, the amount of Compound No. 14 or a pharmaceutically acceptable salt thereof that is administered on each day of dosing is about 6 mg. In some embodiments, the amount of Compound No. 14 or a pharmaceutically acceptable salt thereof that is administered on each day of dosing is about 8 mg. In some embodiments, the amount of Compound No. 14 or a pharmaceutically acceptable salt thereof that is administered on each day of dosing is about 10 mg. In some embodiments, the amount of Compound No. 14 or a pharmaceutically acceptable salt thereof that is administered on each day of dosing is about 12 mg. In some embodiments, the amount of Compound No. 14 or a pharmaceutically acceptable salt thereof that is administered on each day of dosing is about 16 mg. In some embodiments, the amount of Compound No. 14 or a pharmaceutically acceptable salt thereof that is administered on each day of dosing is about 20 mg. In some embodiments, the amount of Compound No. 14 or a pharmaceutically acceptable salt thereof that is administered on each day of dosing is about 30 mg. In some embodiments, the amount of Compound No. 14 or a pharmaceutically acceptable salt thereof that is administered on each day of dosing is about 40 mg. In some embodiments, the amount of Compound No. 14 or a pharmaceutically acceptable salt thereof that is administered on each day of dosing is about 50 mg. In some embodiments, the amount of Compound No. 14 or a pharmaceutically acceptable salt thereof that is administered on each day of dosing is about 60 mg. In some embodiments, the amount of Compound No. 14 or a pharmaceutically acceptable salt thereof that is administered on each day of dosing is about 70 mg. In some embodiments, the amount of Compound No. 14 or a pharmaceutically acceptable salt thereof that is administered on each day of dosing is about 80 mg. In some embodiments, the amount of Compound No. 14 or a pharmaceutically acceptable salt thereof that is administered on each day of dosing is about 90 mg. In some embodiments, the amount of Compound No. 14 or a pharmaceutically acceptable salt thereof that is administered on each day of dosing is about 100 mg. In some embodiments, the amount of Compound No. 14 or a pharmaceutically acceptable salt thereof that is administered on each day of dosing is about 150 mg. In some embodiments, the amount of Compound No. 14 or a pharmaceutically acceptable salt thereof that is administered on each day of dosing is about 200 mg. In some embodiments, the amount of Compound No. 14 or a pharmaceutically acceptable salt thereof that is administered on each day of dosing is about 250 mg. In some embodiments, the amount of Compound No. 14 or a pharmaceutically acceptable salt thereof that is administered on each day of dosing is about 300 mg. In some embodiments, the amount of Compound No. 14 or a pharmaceutically acceptable salt thereof that is administered on each day of dosing is about 350 mg. In some embodiments, the amount of Compound No. 14 or a pharmaceutically acceptable salt thereof that is administered on each day of dosing is about 400 mg. In some embodiments, the amount of Compound No. 14 or a pharmaceutically acceptable salt thereof that is administered on each day of dosing is about 450 mg. In some embodiments, the amount of Compound No. 14 or a pharmaceutically acceptable salt thereof that is administered on each day of dosing is about 500 mg. All dosing amounts refer to the amount of Compound No. 14 administered, and do not include the weight amount of any pharmaceutically acceptable salt.

In some embodiments, the amount of Compound No. 14 or a pharmaceutically acceptable salt thereof that is administered on each day of dosing is from about 0.1 mg to about 3.5 mg. In some embodiments, the amount of Compound No. 14 or a pharmaceutically acceptable salt thereof that is administered on each day of dosing is from about 0.2 mg to about 3.5 mg. In some embodiments, the amount of Compound No. 14 or a pharmaceutically acceptable salt thereof that is administered on each day of dosing is about 0.1 mg. In some embodiments, the amount of Compound No. 14 or a pharmaceutically acceptable salt thereof that is administered on each day of dosing is about 0.2 mg. In some embodiments, the amount of Compound No. 14 or a pharmaceutically acceptable salt thereof that is administered on each day of dosing is about 0.4 mg. In some embodiments, the amount of Compound No. 14 or a pharmaceutically acceptable salt thereof that is administered on each day of dosing is about 0.8 mg. In some embodiments, the amount of Compound No. 14 or a pharmaceutically acceptable salt thereof that is administered on each day of dosing is about 1.2 mg. In some embodiments, the amount of Compound No. 14 or a pharmaceutically acceptable salt thereof that is administered on each day of dosing is about 1.8 mg. In some embodiments, the amount of Compound No. 14 or a pharmaceutically acceptable salt thereof that is administered on each day of dosing is about 2.25 mg. In some embodiments, the amount of Compound No. 14 or a pharmaceutically acceptable salt thereof that is administered on each day of dosing is about 2.8 mg. In some embodiments, the amount of Compound No. 14 or a pharmaceutically acceptable salt thereof that is administered on each day of dosing is about 3.5 mg.

In some embodiments, the amount of Compound No. 14 or a pharmaceutically acceptable salt thereof that is administered on each day of dosing is about 0.01 mg/kg to about 100 mg/kg. In some embodiments, the amount of Compound No. 14 or a pharmaceutically acceptable salt thereof that is administered on each day of dosing is about 0.01 mg/kg to about 50 mg/kg. In some embodiments, the amount of Compound No. 14 or a pharmaceutically acceptable salt thereof that is administered on each day of dosing is about 0.01 mg/kg to about 20 mg/kg.

In some embodiments, the amount of Compound No. 14 or a pharmaceutically acceptable salt thereof that is administered on each day of dosing is about 0.01 mg/kg. In some embodiments, the amount of Compound No. 14 or a pharmaceutically acceptable salt thereof that is administered on each day of dosing is about 0.05 mg/kg. In some embodiments, the amount of Compound No. 14 or a pharmaceutically acceptable salt thereof that is administered on each day of dosing is about 0.1 mg/kg. In some embodiments, the amount of Compound No. 14 or a pharmaceutically acceptable salt thereof that is administered on each day of dosing is about 1 mg/kg. In some embodiments, the amount of Compound No. 14 or a pharmaceutically acceptable salt thereof that is administered on each day of dosing is about 2 mg/kg. In some embodiments, the amount of Compound No. 14 or a pharmaceutically acceptable salt thereof that is administered on each day of dosing is about 4 mg/kg. In some embodiments, the amount of Compound No. 14 or a pharmaceutically acceptable salt thereof that is administered on each day of dosing is about 6 mg/kg. In some embodiments, the amount of Compound No. 14 or a pharmaceutically acceptable salt thereof that is administered on each day of dosing is about 8 mg/kg. In some embodiments, the amount of Compound No. 14 or a pharmaceutically acceptable salt thereof that is administered on each day of dosing is about 10 mg/kg. In some embodiments, the amount of Compound No. 14 or a pharmaceutically acceptable salt thereof that is administered on each day of dosing is about 12 mg/kg. In some embodiments, the amount of Compound No. 14 or a pharmaceutically acceptable salt thereof that is administered on each day of dosing is about 14 mg/kg. In some embodiments, the amount of Compound No. 14 or a pharmaceutically acceptable salt thereof that is administered on each day of dosing is about 16 mg/kg. In some embodiments, the amount of Compound No. 14 or a pharmaceutically acceptable salt thereof that is administered on each day of dosing is about 18 mg/kg. In some embodiments, the amount of Compound No. 14 or a pharmaceutically acceptable salt thereof that is administered on each day of dosing is about 20 mg/kg. In some embodiments, the amount of Compound No. 14 or a pharmaceutically acceptable salt thereof that is administered on each day of dosing is about 30 mg/kg. In some embodiments, the amount of Compound No. 14 or a pharmaceutically acceptable salt thereof that is administered on each day of dosing is about 40 mg/kg. In some embodiments, the amount of Compound No. 14 or a pharmaceutically acceptable salt thereof that is administered on each day of dosing is about 50 mg/kg. In some embodiments, the amount of Compound No. 14 or a pharmaceutically acceptable salt thereof that is administered on each day of dosing is about 60 mg/kg. In some embodiments, the amount of Compound No. 14 or a pharmaceutically acceptable salt thereof that is administered on each day of dosing is about 70 mg/kg. In some embodiments, the amount of Compound No. 14 or a pharmaceutically acceptable salt thereof that is administered on each day of dosing is about 80 mg/kg. In some embodiments, the amount of Compound No. 14 or a pharmaceutically acceptable salt thereof that is administered on each day of dosing is about 90 mg/kg. In some embodiments, the amount of Compound No. 14 or a pharmaceutically acceptable salt thereof that is administered on each day of dosing is about 100 mg/kg.

In some embodiments, the checkpoint inhibitor is administered on a daily schedule. In some embodiments, the checkpoint inhibitor is administered every other day. In some embodiments, the checkpoint inhibitor is administered once every three days. In some embodiments, the checkpoint inhibitor is administered on a twice-weekly schedule. In some embodiments, the checkpoint inhibitor is administered on a three times a week schedule. In some embodiments, the checkpoint inhibitor is administered on a weekly schedule. In some embodiments, the checkpoint inhibitor is administered on a once every two weeks schedule. In some embodiments, the checkpoint inhibitor is administered on a once every three weeks schedule. In some embodiments, the checkpoint inhibitor is administered on a once every four weeks schedule. In some embodiments, the checkpoint inhibitor is administered on a once every eight weeks schedule. In some embodiments, the checkpoint inhibitor is administered on a once every twelve weeks schedule.

In some embodiments, the checkpoint inhibitor is administered at least 3 times on alternate days within a 7-day cycle. In some embodiments, the checkpoint inhibitor is administered on day 1 of a treatment cycle. In some embodiments, the checkpoint inhibitor is administered on day 1 and day 4 of a 7-day cycle. In some embodiments, the checkpoint inhibitor is administered on consecutive days in a 7-day cycle followed by an intermission. In some embodiments, the checkpoint inhibitor is administered for 2 consecutive days followed by an intermission of 5 consecutive days for at least one 7-day cycle. In some embodiments, the checkpoint inhibitor is administered for 3 consecutive days followed by an intermission of 4 consecutive days for at least one 7-day cycle. In some embodiments, the checkpoint inhibitor is administered for 4 consecutive days followed by an intermission of 3 consecutive days for at least one 7-day cycle. In some embodiments, the checkpoint inhibitor is administered for 5 consecutive days followed by an intermission of 2 consecutive days for at least one 7-day cycle.

In some embodiments, the checkpoint inhibitor is administered on day 1 of a 21-day treatment cycle. In some embodiments, the checkpoint inhibitor is administered on day 2 of a 21-day treatment cycle. In some embodiments, the checkpoint inhibitor is administered on day 2 of a first 21-day treatment cycle and on day 1 of each subsequent 21-day treatment cycle.

The present description contemplates administration of the checkpoint inhibitor for one or more treatment cycles, for example, 1, 2, 3, 4, 5, 6, or more, treatment cycles. In some embodiments, a treatment cycle is about 7 days to about 84 days, or more. In some embodiments, a treatment cycle is 7 days, 14 days, 21 days, 28 days, 35 days, 42 days, 49 days, 56 days, or 84 days. In some embodiments, a treatment cycle is 21 days or 28 days. In some embodiments, there will be periods of rest within or between one or more of the treatment cycles. For example, in some embodiments, there will be a period of rest at the end of the treatment cycle. In some embodiments, there will be a period of rest between the second and third treatment cycle but not the first and second treatment cycle. In another embodiment, there might be a period of rest between the first and second treatment cycle but not the second and third treatment cycle. Dosing schedules include, for example, administering the checkpoint inhibitor once during a treatment schedule, e.g., on day 1 of a 21 day cycle, twice during a treatment cycle, e.g., on days 1 and 15 of a 21 day cycle or on days 1 and 15 of a 28 day cycle, three times during a treatment cycle, e.g., on days 1, 8 and 15 of a 21 day cycle or on days 1, 8 and 15 of a 28 day cycle, and four times during a treatment cycle, e.g., on days 1, 4, 8, and 11 of a 21 day cycle or of on days 1, 4, 8, and 11 of a 28 day cycle. Other dosage schedules are encompassed by the present invention.

In some embodiments, the checkpoint inhibitor is administered by subcutaneous injection. In some embodiments, the checkpoint inhibitor is administered by intravenous infusion followed by one or more subsequent subcutaneous injections. In some embodiments, the intravenous infusion and one or more subsequent subcutaneous injections are administered according to the dosing schedules and methods disclosed herein.

In some embodiments, both Compound No. 14 and the checkpoint inhibitor are administered on day 1 of a 21-day treatment cycle. In some embodiments, Compound No. 14 is administered first on day 1 of a 21-day treatment cycle followed by the checkpoint inhibitor. In some embodiments, Compound No. 14 is administered on day 1 of a 21-day treatment cycle and the checkpoint inhibitor is administered on day 1 of a 21-day treatment cycle 1 hour after administration Compound No. 14.

In some embodiments, Compound No. 14 is administered as a 60±10-minute intravenous infusion.

In some embodiments, the amount of the anti-PD-1 antibody that is administered on each day of dosing is about 0.5 mg to about 1000 mg. In some embodiments, the amount of the anti-PD-1 antibody that is administered on each day of dosing is about 0.5 mg to about 900 mg. In some embodiments, the amount of the anti-PD-1 antibody that is administered on each day of dosing is about 0.5 mg to about 800 mg. In some embodiments, the amount of the anti-PD-1 antibody that is administered on each day of dosing is about 0.5 mg to about 700 mg. In some embodiments, the amount of the anti-PD-1 antibody that is administered on each day of dosing is about 0.5 mg to about 600 mg. In some embodiments, the amount of the anti-PD-1 antibody that is administered on each day of dosing is about 0.5 mg to about 500 mg. In some embodiments, the amount of the anti-PD-1 antibody that is administered on each day of dosing is about 1 mg to about 500 mg. In some embodiments, the amount of the anti-PD-1 antibody that is administered on each day of dosing is about 10 mg to about 500 mg. In some embodiments, the amount of the anti-PD-1 antibody that is administered on each day of dosing is about 50 mg to about 500 mg. In some embodiments, the amount of the anti-PD-1 antibody that is administered on each day of dosing is about 100 mg to about 500 mg. In some embodiments, the amount of the anti-PD-1 antibody that is administered on each day of dosing is about 150 mg to about 500 mg. In some embodiments, the amount of the anti-PD-1 antibody that is administered on each day of dosing is about 200 mg to about 500 mg. In some embodiments, the amount of the anti-PD-1 antibody that is administered on each day of dosing is about 220 mg to about 500 mg. In some embodiments, the amount of the anti-PD-1 antibody that is administered on each day of dosing is about 240 mg to about 500 mg. In some embodiments, the amount of the anti-PD-1 antibody that is administered on each day of dosing is about 260 mg to about 500 mg. In some embodiments, the amount of the anti-PD-1 antibody that is administered on each day of dosing is about 280 mg to about 500 mg. In some embodiments, the amount of the anti-PD-1 antibody that is administered on each day of dosing is about 300 mg to about 500 mg. In some embodiments, the amount of the anti-PD-1 antibody that is administered on each day of dosing is about 320 mg to about 500 mg. In some embodiments, the amount of the anti-PD-1 antibody that is administered on each day of dosing is about 340 mg to about 500 mg. In some embodiments, the amount of the anti-PD-1 antibody that is administered on each day of dosing is about 360 mg to about 500 mg. In some embodiments, the amount of the anti-PD-1 antibody that is administered on each day of dosing is about 380 mg to about 500 mg. In some embodiments, the amount of the anti-PD-1 antibody that is administered on each day of dosing is about 400 mg to about 500 mg. In some embodiments, the amount of the anti-PD-1 antibody that is administered on each day of dosing is about 200 mg to about 480 mg. In some embodiments, the amount of the anti-PD-1 antibody that is administered on each day of dosing is about 200 mg to about 460 mg. In some embodiments, the amount of the anti-PD-1 antibody that is administered on each day of dosing is about 200 mg to about 440 mg. In some embodiments, the amount of the anti-PD-1 antibody that is administered on each day of dosing is about 200 mg to about 420 mg. In some embodiments, the amount of the anti-PD-1 antibody that is administered on each day of dosing is about 200 mg to about 400 mg. In some embodiments, the amount of the anti-PD-1 antibody that is administered on each day of dosing is about 200 mg to about 380 mg. In some embodiments, the amount of the anti-PD-1 antibody that is administered on each day of dosing is about 200 mg to about 360 mg. In some embodiments, the amount of the anti-PD-1 antibody that is administered on each day of dosing is about 200 mg to about 340 mg. In some embodiments, the amount of the anti-PD-1 antibody that is administered on each day of dosing is about 200 mg to about 320 mg. In some embodiments, the amount of the anti-PD-1 antibody that is administered on each day of dosing is about 200 mg to about 300 mg.

In some embodiments, the amount of the anti-PD-1 antibody that is administered on each day of dosing is about 100 mg. In some embodiments, the amount of the anti-PD-1 antibody that is administered on each day of dosing is about 120 mg. In some embodiments, the amount of the anti-PD-1 antibody that is administered on each day of dosing is about 140 mg. In some embodiments, the amount of the anti-PD-1 antibody that is administered on each day of dosing is about 160 mg. In some embodiments, the amount of the anti-PD-1 antibody that is administered on each day of dosing is about 180 mg. In some embodiments, the amount of the anti-PD-1 antibody that is administered on each day of dosing is about 200 mg. In some embodiments, the amount of the anti-PD-1 antibody that is administered on each day of dosing is about 220 mg. In some embodiments, the amount of the anti-PD-1 antibody that is administered on each day of dosing is about 240 mg. In some embodiments, the amount of the anti-PD-1 antibody that is administered on each day of dosing is about 260 mg. In some embodiments, the amount of the anti-PD-1 antibody that is administered on each day of dosing is about 280 mg. In some embodiments, the amount of the anti-PD-1 antibody that is administered on each day of dosing is about 300 mg. In some embodiments, the amount of the anti-PD-1 antibody that is administered on each day of dosing is about 320 mg. In some embodiments, the amount of the anti-PD-1 antibody that is administered on each day of dosing is about 340 mg. In some embodiments, the amount of the anti-PD-1 antibody that is administered on each day of dosing is about 360 mg. In some embodiments, the amount of the anti-PD-1 antibody that is administered on each day of dosing is about 380 mg. In some embodiments, the amount of the anti-PD-1 antibody that is administered on each day of dosing is about 400 mg. In some embodiments, the amount of the anti-PD-1 antibody that is administered on each day of dosing is about 420 mg. In some embodiments, the amount of the anti-PD-1 antibody that is administered on each day of dosing is about 440 mg. In some embodiments, the amount of the anti-PD-1 antibody that is administered on each day of dosing is about 460 mg. In some embodiments, the amount of the anti-PD-1 antibody that is administered on each day of dosing is about 480 mg. In some embodiments, the amount of the anti-PD-1 antibody that is administered on each day of dosing is about 500 mg. In some embodiments, the amount of the anti-PD-1 antibody that is administered on each day of dosing is about 600 mg. In some embodiments, the amount of the anti-PD-1 antibody that is administered on each day of dosing is about 700 mg. In some embodiments, the amount of the anti-PD-1 antibody that is administered on each day of dosing is about 800 mg. In some embodiments, the amount of the anti-PD-1 antibody that is administered on each day of dosing is about 900 mg. In some embodiments, the amount of the anti-PD-1 antibody that is administered on each day of dosing is about 1000 mg.

In some embodiments, the amount of the anti-PD-1 antibody that is administered on each day of dosing is about 200 mg.

In some embodiments, the amount of the anti-PD-1 antibody that is administered on each day of dosing is about 0.5 mg/kg to about 10 mg/kg. In some embodiments, the amount of the anti-PD-1 antibody that is administered on each day of dosing is about 0.5 mg/kg to about 7.5 mg/kg. In some embodiments, the amount of the anti-PD-1 antibody that is administered on each day of dosing is about 0.5 mg/kg to about 5 mg/kg. In some embodiments, the amount of the anti-PD-1 antibody that is administered on each day of dosing is about 1 mg/kg to about 4 mg/kg. In some embodiments, the amount of the anti-PD-1 antibody that is administered on each day of dosing is about 1 mg/kg to about 3 mg/kg. In some embodiments, the amount of the anti-PD-1 antibody that is administered on each day of dosing is about 0.5 mg/kg. In some embodiments, the amount of the anti-PD-1 antibody that is administered on each day of dosing is about 1 mg/kg. In some embodiments, the amount of the anti-PD-1 antibody that is administered on each day of dosing is about 1.5 mg/kg. In some embodiments, the amount of the anti-PD-1 antibody that is administered on each day of dosing is about 2 mg/kg. In some embodiments, the amount of the anti-PD-1 antibody that is administered on each day of dosing is about 2.5 mg/kg. In some embodiments, the amount of the anti-PD-1 antibody that is administered on each day of dosing is about 3 mg/kg. In some embodiments, the amount of the anti-PD-1 antibody that is administered on each day of dosing is about 3.5 mg/kg. In some embodiments, the amount of the anti-PD-1 antibody that is administered on each day of dosing is about 4 mg/kg. In some embodiments, the amount of the anti-PD-1 antibody that is administered on each day of dosing is about 4.5 mg/kg. In some embodiments, the amount of the anti-PD-1 antibody that is administered on each day of dosing is about 5 mg/kg. In some embodiments, the amount of the anti-PD-1 antibody that is administered on each day of dosing is about 7.5 mg/kg. In some embodiments, the amount of the anti-PD-1 antibody that is administered on each day of dosing is about 10 mg/kg.

In some embodiments, the anti-PD-1 antibody is nivolumab, or a pharmaceutically acceptable salt thereof. In some embodiments, the anti-PD-1 antibody is pembrolizumab, or a pharmaceutically acceptable salt thereof. In some embodiments, the anti-PD-1 antibody is cemiplimab, or a pharmaceutically acceptable salt thereof.

In some embodiments, the administration of nivolumab, pembrolizumab, and cemiplimab is in accordance with its prescribing information as approved by the health authorities, such as those issued by the FDA, or the EMA, which are incorporated here by their entirety.

In some embodiments, the anti-PD-1 antibody is pembrolizumab, or a pharmaceutically acceptable salt thereof. In some embodiments, the amount of the pembrolizumab that is administered on each day of dosing is about 200 mg. In some embodiments, the pembrolizumab is administered on day 1 of a 21 day cycle in an amount of 200 mg.

In some embodiments, the anti-PD-1 antibody is pembrolizumab, or a pharmaceutically acceptable salt thereof, and the pembrolizumab is administered in combination with Compound No. 14. In some embodiments, the pembrolizumab is administered on day 1 of a 21-day cycle and Compound No. 14 is administered on days 1, 8, and 15 of a 21-day cycle. In some embodiments, the pembrolizumab is administered in an amount of 200 mg on day 1 of a 21-day cycle and Compound No. 14 is administered in an amount of 0.1 mg on days 1, 8, and 15 of a 21-day cycle. In some embodiments, the pembrolizumab is administered in an amount of 200 mg on day 1 of a 21-day cycle and Compound No. 14 is administered in an amount of 0.2 mg on days 1, 8, and 15 of a 21-day cycle. In some embodiments, the pembrolizumab is administered in an amount of 200 mg on day 1 of a 21-day cycle and Compound No. 14 is administered in an amount of 0.2 mg or higher on days 1, 8, and 15 of a 21-day cycle. In some embodiments, the pembrolizumab is administered in an amount of 200 mg on day 1 of a 21-day cycle and Compound No. 14 is administered in an amount of from 0.1 mg to 3.5 mg on days 1, 8, and 15 of a 21-day cycle. In some embodiments, the pembrolizumab is administered in an amount of 200 mg on day 1 of a 21-day cycle and Compound No. 14 is administered in an amount of from 0.1 mg to 1.2 mg on days 1, 8, and 15 of a 21-day cycle. In some embodiments, the pembrolizumab is administered in an amount of 200 mg on day 1 of a 21-day cycle and Compound No. 14 is administered in an amount of from 0.2 mg to 3.5 mg on days 1, 8, and 15 of a 21-day cycle. In some embodiments, the pembrolizumab is administered in an amount of 200 mg on day 1 of a 21-day cycle and Compound No. 14 is administered in an amount of from 0.2 mg to 1.2 mg on days 1, 8, and 15 of a 21-day cycle. In some embodiments, the pembrolizumab is administered in an amount of 200 mg on day 1 of a 21-day cycle and Compound No. 14 is administered in an amount of 0.1 mg, 0.2 mg, 0.4 mg, 0.8 mg, 1.2 mg, 1.6 mg, 2.0 mg, 2.5 mg, 3.0 mg, or 3.5 mg on days 1, 8, and 15 of a 21-day cycle.

In some embodiments, the amount of the anti-PD-L1 antibody that is administered on each day of dosing is about 0.5 mg to about 2000 mg. In some embodiments, the amount of the anti-PD-L1 antibody that is administered on each day of dosing is about 0.5 mg to about 1800 mg. In some embodiments, the amount of the anti-PD-L1 antibody that is administered on each day of dosing is about 0.5 mg to about 1600 mg. In some embodiments, the amount of the anti-PD-L1 antibody that is administered on each day of dosing is about 0.5 mg to about 1400 mg. In some embodiments, the amount of the anti-PD-L1 antibody that is administered on each day of dosing is about 0.5 mg to about 1200 mg. In some embodiments, the amount of the anti-PD-L1 antibody that is administered on each day of dosing is about 0.5 mg to about 1000 mg. In some embodiments, the amount of the anti-PD-L1 antibody that is administered on each day of dosing is about 1 mg to about 2000 mg. In some embodiments, the amount of the anti-PD-L1 antibody that is administered on each day of dosing is about 10 mg to about 2000 mg. In some embodiments, the amount of the anti-PD-L1 antibody that is administered on each day of dosing is about 100 mg to about 2000 mg. In some embodiments, the amount of the anti-PD-L1 antibody that is administered on each day of dosing is about 200 mg to about 2000 mg. In some embodiments, the amount of the anti-PD-L1 antibody that is administered on each day of dosing is about 400 mg to about 2000 mg. In some embodiments, the amount of the anti-PD-L1 antibody that is administered on each day of dosing is about 600 mg to about 2000 mg. In some embodiments, the amount of the anti-PD-L1 antibody that is administered on each day of dosing is about 800 mg to about 2000 mg. In some embodiments, the amount of the anti-PD-L1 antibody that is administered on each day of dosing is about 1000 mg to about 2000 mg. In some embodiments, the amount of the anti-PD-L1 antibody that is administered on each day of dosing is about 1200 mg to about 2000 mg. In some embodiments, the amount of the anti-PD-L1 antibody that is administered on each day of dosing is about 1500 mg to about 2000 mg. In some embodiments, the amount of the anti-PD-L1 antibody that is administered on each day of dosing is about 1000 mg to about 2000 mg. In some embodiments, the amount of the anti-PD-L1 antibody that is administered on each day of dosing is about 1000 mg to about 1800 mg. In some embodiments, the amount of the anti-PD-L1 antibody that is administered on each day of dosing is about 1000 mg to about 1600 mg. In some embodiments, the amount of the anti-PD-L1 antibody that is administered on each day of dosing is about 1000 mg to about 1400 mg. In some embodiments, the amount of the anti-PD-L1 antibody that is administered on each day of dosing is about 1000 mg to about 1200 mg. In some embodiments, the amount of the anti-PD-L1 antibody that is administered on each day of dosing is about 1200 mg to about 1400 mg. In some embodiments, the amount of the anti-PD-L1 antibody that is administered on each day of dosing is about 1100 mg to about 1300 mg. In some embodiments, the amount of the anti-PD-L1 antibody that is administered on each day of dosing is about 1100 mg to about 1200 mg. In some embodiments, the amount of the anti-PD-L1 antibody that is administered on each day of dosing is about 1200 mg to about 1300 mg.

In some embodiments, the amount of the anti-PD-L1 antibody that is administered on each day of dosing is about 100 mg. In some embodiments, the amount of the anti-PD-L1 antibody that is administered on each day of dosing is about 200 mg. In some embodiments, the amount of the anti-PD-L1 antibody that is administered on each day of dosing is about 300 mg. In some embodiments, the amount of the anti-PD-L1 antibody that is administered on each day of dosing is about 400 mg. In some embodiments, the amount of the anti-PD-L1 antibody that is administered on each day of dosing is about 500 mg. In some embodiments, the amount of the anti-PD-L1 antibody that is administered on each day of dosing is about 600 mg. In some embodiments, the amount of the anti-PD-L1 antibody that is administered on each day of dosing is about 700 mg. In some embodiments, the amount of the anti-PD-L1 antibody that is administered on each day of dosing is about 800 mg. In some embodiments, the amount of the anti-PD-L1 antibody that is administered on each day of dosing is about 900 mg. In some embodiments, the amount of the anti-PD-L1 antibody that is administered on each day of dosing is about 1000 mg. In some embodiments, the amount of the anti-PD-L1 antibody that is administered on each day of dosing is about 1100 mg. In some embodiments, the amount of the anti-PD-L1 antibody that is administered on each day of dosing is about 1200 mg. In some embodiments, the amount of the anti-PD-L1 antibody that is administered on each day of dosing is about 1300 mg. In some embodiments, the amount of the anti-PD-L1 antibody that is administered on each day of dosing is about 1400 mg. In some embodiments, the amount of the anti-PD-L1 antibody that is administered on each day of dosing is about 1500 mg. In some embodiments, the amount of the anti-PD-L1 antibody that is administered on each day of dosing is about 1600 mg. In some embodiments, the amount of the anti-PD-L1 antibody that is administered on each day of dosing is about 1700 mg. In some embodiments, the amount of the anti-PD-L1 antibody that is administered on each day of dosing is about 1800 mg. In some embodiments, the amount of the anti-PD-L1 antibody that is administered on each day of dosing is about 1900 mg. In some embodiments, the amount of the anti-PD-L1 antibody that is administered on each day of dosing is about 2000 mg. In some embodiments, the amount of the anti-PD-L1 antibody that is administered on each day of dosing is about 2500 mg. In some embodiments, the amount of the anti-PD-L1 antibody that is administered on each day of dosing is about 3000 mg.

In some embodiments, the amount of the anti-PD-L1 antibody that is administered on each day of dosing is about 0.5 mg/kg to about 20 mg/kg. In some embodiments, the amount of the anti-PD-L1 antibody that is administered on each day of dosing is about 1 mg/kg to about 20 mg/kg. In some embodiments, the amount of the anti-PD-L1 antibody that is administered on each day of dosing is about 5 mg/kg to about 20 mg/kg. In some embodiments, the amount of the anti-PD-L1 antibody that is administered on each day of dosing is about 5 mg/kg to about 15 mg/kg. In some embodiments, the amount of the anti-PD-L1 antibody that is administered on each day of dosing is about 5 mg/kg to about 10 mg/kg. In some embodiments, the amount of the anti-PD-L1 antibody that is administered on each day of dosing is about 6 mg/kg to about 10 mg/kg. In some embodiments, the amount of the anti-PD-L1 antibody that is administered on each day of dosing is about 7 mg/kg to about 10 mg/kg. In some embodiments, the amount of the anti-PD-L1 antibody that is administered on each day of dosing is about 8 mg/kg to about 10 mg/kg. In some embodiments, the amount of the anti-PD-L1 antibody that is administered on each day of dosing is about 9 mg/kg to about 10 mg/kg. In some embodiments, the amount of the anti-PD-L1 antibody that is administered on each day of dosing is about 10 mg/kg to about 15 mg/kg. In some embodiments, the amount of the anti-PD-L1 antibody that is administered on each day of dosing is about 10 mg/kg to about 14 mg/kg. In some embodiments, the amount of the anti-PD-L1 antibody that is administered on each day of dosing is about 10 mg/kg to about 13 mg/kg. In some embodiments, the amount of the anti-PD-L1 antibody that is administered on each day of dosing is about 10 mg/kg to about 12 mg/kg. In some embodiments, the amount of the anti-PD-L1 antibody that is administered on each day of dosing is about 10 mg/kg to about 11 mg/kg. In some embodiments, the amount of the anti-PD-L1 antibody that is administered on each day of dosing is about 1 mg/kg. In some embodiments, the amount of the anti-PD-L1 antibody that is administered on each day of dosing is about 2 mg/kg. In some embodiments, the amount of the anti-PD-L1 antibody that is administered on each day of dosing is about 3 mg/kg. In some embodiments, the amount of the anti-PD-L1 antibody that is administered on each day of dosing is about 4 mg/kg. In some embodiments, the amount of the anti-PD-L1 antibody that is administered on each day of dosing is about 5 mg/kg. In some embodiments, the amount of the anti-PD-L1 antibody that is administered on each day of dosing is about 6 mg/kg. In some embodiments, the amount of the anti-PD-L1 antibody that is administered on each day of dosing is about 7 mg/kg. In some embodiments, the amount of the anti-PD-L1 antibody that is administered on each day of dosing is about 8 mg/kg. In some embodiments, the amount of the anti-PD-L1 antibody that is administered on each day of dosing is about 9 mg/kg. In some embodiments, the amount of the anti-PD-L1 antibody that is administered on each day of dosing is about 10 mg/kg. In some embodiments, the amount of the anti-PD-L1 antibody that is administered on each day of dosing is about 11 mg/kg. In some embodiments, the amount of the anti-PD-L1 antibody that is administered on each day of dosing is about 12 mg/kg. In some embodiments, the amount of the anti-PD-L1 antibody that is administered on each day of dosing is about 13 mg/kg. In some embodiments, the amount of the anti-PD-L1 antibody that is administered on each day of dosing is about 14 mg/kg. In some embodiments, the amount of the anti-PD-L1 antibody that is administered on each day of dosing is about 15 mg/kg. In some embodiments, the amount of the anti-PD-L1 antibody that is administered on each day of dosing is about 16 mg/kg. In some embodiments, the amount of the anti-PD-L1 antibody that is administered on each day of dosing is about 17 mg/kg. In some embodiments, the amount of the anti-PD-L1 antibody that is administered on each day of dosing is about 18 mg/kg. In some embodiments, the amount of the anti-PD-L1 antibody that is administered on each day of dosing is about 19 mg/kg. In some embodiments, the amount of the anti-PD-L1 antibody that is administered on each day of dosing is about 20 mg/kg.

In some embodiments, the anti-PD-L1 antibody is atezolizumab, or a pharmaceutically acceptable salt thereof. In some embodiments, the anti-PD-L1 antibody is durvalumab, or a pharmaceutically acceptable salt thereof. In some embodiments, the anti-PD-L1 antibody is avelumab, or a pharmaceutically acceptable salt thereof.

In some embodiments, the administration of atezolizumab, durvalumab, and avelumab is in accordance with its prescribing information as approved by the health authorities, such as those issued by the FDA, or the EMA, which are incorporated here by their entirety.

In some embodiments, the amount of the anti-CTLA-4 antibody that is administered on each day of dosing is about 0.5 mg to about 2000 mg. In some embodiments, the amount of the anti-CTLA-4 antibody that is administered on each day of dosing is about 1 mg to about 2000 mg. In some embodiments, the amount of the anti-CTLA-4 antibody that is administered on each day of dosing is about 10 mg to about 2000 mg. In some embodiments, the amount of the anti-CTLA-4 antibody that is administered on each day of dosing is about 50 mg to about 2000 mg. In some embodiments, the amount of the anti-CTLA-4 antibody that is administered on each day of dosing is about 100 mg to about 2000 mg. In some embodiments, the amount of the anti-CTLA-4 antibody that is administered on each day of dosing is about 1 mg. In some embodiments, the amount of the anti-CTLA-4 antibody that is administered on each day of dosing is about 10 mg. In some embodiments, the amount of the anti-CTLA-4 antibody that is administered on each day of dosing is about 100 mg. In some embodiments, the amount of the anti-CTLA-4 antibody that is administered on each day of dosing is about 200 mg. In some embodiments, the amount of the anti-CTLA-4 antibody that is administered on each day of dosing is about 400 mg. In some embodiments, the amount of the anti-CTLA-4 antibody that is administered on each day of dosing is about 600 mg. In some embodiments, the amount of the anti-CTLA-4 antibody that is administered on each day of dosing is about 800 mg. In some embodiments, the amount of the anti-CTLA-4 antibody that is administered on each day of dosing is about 1000 mg. In some embodiments, the amount of the anti-CTLA-4 antibody that is administered on each day of dosing is about 1200 mg. In some embodiments, the amount of the anti-CTLA-4 antibody that is administered on each day of dosing is about 1400 mg. In some embodiments, the amount of the anti-CTLA-4 antibody that is administered on each day of dosing is about 1600 mg. In some embodiments, the amount of the anti-CTLA-4 antibody that is administered on each day of dosing is about 1800 mg. In some embodiments, the amount of the anti-CTLA-4 antibody that is administered on each day of dosing is about 2000 mg.

In some embodiments, the amount of the anti-CTLA-4 antibody that is administered on each day of dosing is about 0.5 mg/kg to about 20 mg/kg. In some embodiments, the amount of the anti-CTLA-4 antibody that is administered on each day of dosing is about 1 mg/kg to about 20 mg/kg. In some embodiments, the amount of the anti-CTLA-4 antibody that is administered on each day of dosing is about 1 mg/kg to about 18 mg/kg. In some embodiments, the amount of the anti-CTLA-4 antibody that is administered on each day of dosing is about 1 mg/kg to about 16 mg/kg. In some embodiments, the amount of the anti-CTLA-4 antibody that is administered on each day of dosing is about 1 mg/kg to about 14 mg/kg. In some embodiments, the amount of the anti-CTLA-4 antibody that is administered on each day of dosing is about 1 mg/kg to about 12 mg/kg. In some embodiments, the amount of the anti-CTLA-4 antibody that is administered on each day of dosing is about 1 mg/kg to about 10 mg/kg. In some embodiments, the amount of the anti-CTLA-4 antibody that is administered on each day of dosing is about 1 mg/kg. In some embodiments, the amount of the anti-CTLA-4 antibody that is administered on each day of dosing is about 2 mg/kg. In some embodiments, the amount of the anti-CTLA-4 antibody that is administered on each day of dosing is about 3 mg/kg. In some embodiments, the amount of the anti-CTLA-4 antibody that is administered on each day of dosing is about 4 mg/kg. In some embodiments, the amount of the anti-CTLA-4 antibody that is administered on each day of dosing is about 5 mg/kg. In some embodiments, the amount of the anti-CTLA-4 antibody that is administered on each day of dosing is about 6 mg/kg. In some embodiments, the amount of the anti-CTLA-4 antibody that is administered on each day of dosing is about 7 mg/kg. In some embodiments, the amount of the anti-CTLA-4 antibody that is administered on each day of dosing is about 8 mg/kg. In some embodiments, the amount of the anti-CTLA-4 antibody that is administered on each day of dosing is about 9 mg/kg. In some embodiments, the amount of the anti-CTLA-4 antibody that is administered on each day of dosing is about 10 mg/kg. In some embodiments, the amount of the anti-CTLA-4 antibody that is administered on each day of dosing is about 11 mg/kg. In some embodiments, the amount of the anti-CTLA-4 antibody that is administered on each day of dosing is about 12 mg/kg. In some embodiments, the amount of the anti-CTLA-4 antibody that is administered on each day of dosing is about 13 mg/kg. In some embodiments, the amount of the anti-CTLA-4 antibody that is administered on each day of dosing is about 14 mg/kg. In some embodiments, the amount of the anti-CTLA-4 antibody that is administered on each day of dosing is about 15 mg/kg. In some embodiments, the amount of the anti-CTLA-4 antibody that is administered on each day of dosing is about 16 mg/kg. In some embodiments, the amount of the anti-CTLA-4 antibody that is administered on each day of dosing is about 17 mg/kg. In some embodiments, the amount of the anti-CTLA-4 antibody that is administered on each day of dosing is about 18 mg/kg. In some embodiments, the amount of the anti-CTLA-4 antibody that is administered on each day of dosing is about 19 mg/kg. In some embodiments, the amount of the anti-CTLA-4 antibody that is administered on each day of dosing is about 20 mg/kg.

In some embodiments, the anti-CTLA-4 antibody is ipilimumab, or a pharmaceutically acceptable salt thereof.

In some embodiments, the administration of ipilimumab is in accordance with its prescribing information as approved by the health authorities, such as those issued by the FDA, or the EMA, which are incorporated here by their entirety.

Pharmaceutical Compositions

The STING agonists and the checkpoint inhibitors used in the methods and kits described herein can be formulated into pharmaceutical compositions suitable for administration. The pharmaceutical compositions may comprise pharmaceutically acceptable excipients. A pharmaceutically acceptable excipient, as used herein, includes, but are not limited to, any and all solvents, dispersion media, or other liquid vehicles, dispersion or suspension aids, diluents, granulating and/or dispersing agents, surface active agents, isotonic agents, thickening or emulsifying agents, preservatives, binders, lubricants or oil, coloring, sweetening or flavoring agents, stabilizers, antioxidants, antimicrobial or antifungal agents, osmolality adjusting agents, pH adjusting agents, buffers, chelants, cyoprotectants, and/or bulking agents, as suited to the particular dosage form desired. Various excipients for formulating pharmaceutical compositions and techniques for preparing the composition are known in the art (see Remington: The Science and Practice of Pharmacy, 21$^{st}$ Ed., A. R. Gennaro (Lippincott, Williams & Wilkins, Baltimore, MD), 2006; incorporated by reference in its entirety)

Any of the therapeutic agents described herein may be in the form of a pharmaceutically acceptable salt. In some embodiments, such salts are derived from inorganic or organic acids or bases. For reviews of suitable salts, see, e.g., Berge et al., *J. Pharm. Sci.*, 1977, 66, 1-19 and *Remington: The Science and Practice of Pharmacy*, 20th Ed., A. Gennaro (ed.), Lippincott Williams & Wilkins (2000).

Examples of suitable acid addition salts include acetate, adipate, alginate, aspartate, benzoate, benzene sulfonate, bisulfate, butyrate, citrate, camphorate, camphor sulfonate, cyclopentanepropionate, digluconate, dodecyl sulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Examples of suitable base addition salts include ammonium salts; alkali metal salts, such as sodium and potassium salts; alkaline earth metal salts, such as calcium and magnesium salts; salts with organic bases, such as dicyclohexylamine salts, N-methyl-D-glucamine; and salts with amino acids such as arginine, lysine, and the like.

For example, Berge lists the following FDA-approved commercially marketed salts: anions acetate, besylate (benzenesulfonate), benzoate, bicarbonate, bitartrate, bromide, calcium edetate (ethylenediaminetetraacetate), camsylate (camphorsulfonate), carbonate, chloride, citrate, dihydrochloride, edetate (ethylenediaminetetraacetate), edisylate (1,2-ethanedisulfonate), estolate (lauryl sulfate), esylate (ethanesulfonate), fumarate, gluceptate (glucoheptonate), gluconate, glutamate, glycollylarsanilate (glycollamidophenylarsonate), hexylresorcinate, hydrabamine (N,N'-di(dehydroabietyl)-ethylenediamine), hydrobromide, hydrochloride, hydroxynaphthoate, iodide, isethionate (2-hydroxyethanesulfonate), lactate, lactobionate, malate, maleate, mandelate, mesylate (methanesulfonate), methylbromide, methylnitrate, methylsulfate, mucate, napsylate (2-naphthalenesulfonate), nitrate, pamoate (embonate), pantothenate, phosphate/diphosphate, polygalacturonate, salicylate, stearate, subacetate, succinate, sulfate, tannate, tartrate, teoclate (8-chlorotheophyllinate) and triethiodide; organic cations benzathine (N,N'-dibenzylethylenediamine), chloroprocaine, choline, diethanolamine, ethylenediamine, meglumine (N-methylglucamine) and procaine; and metallic cations aluminum, calcium, lithium, magnesium, potassium, sodium and zinc.

Berge additionally lists the following non-FDA-approved commercially marketed (outside the United States) salts: anions adipate, alginate, aminosalicylate, anhydromethylenecitrate, arecoline, aspartate, bisulfate, butylbromide, camphorate, digluconate, dihydrobromide, disuccinate, glycerophosphate, hemisulfate, hydrofluoride, hydroiodide, methylenebis(salicylate), napadisylate (1,5-naphthalenedisulfonate), oxalate, pectinate, persulfate, phenylethylbarbiturate, picrate, propionate, thiocyanate, tosylate and undecanoate; organic cations benethamine (N-benzylphenethylamine), clemizole (1-p-chlorobenzyl-2-pyrrolildine-1'-ylmethylbenzimidazole), diethylamine, piperazine and tromethamine (tris(hydroxymethyl)aminomethane); and metallic cations barium and bismuth.

The pharmaceutical compositions may comprise pharmaceutically acceptable carriers. As used herein, "pharmaceutically acceptable carrier" refers to a material that is compatible with a recipient subject (a human) and is suitable for delivering an active agent to the target site without terminating the activity of the agent. The toxicity or adverse effects, if any, associated with the carrier preferably are commensurate with a reasonable risk/benefit ratio for the intended use of the active agent.

Pharmaceutically acceptable carriers that may be used in these compositions include ion exchangers, alumina, aluminum stearate, lecithin, serum proteins, such as human serum albumin, buffer substances such as phosphates or carbonates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions for use in the methods of the present disclosure may be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may contain stabilizers, pH modifiers, surfactants, solubilizing agents, bioavailability modifiers and combinations of these. These pharmaceutical compositions are formulated for pharmaceutical administration to a human being. Such compositions may be administered orally, parenterally, by inhalation spray, topically, rectally, nasally, buccally, vaginally or via an implanted reservoir. The term "parenteral" as used herein includes subcutaneous, intravenous, intraperitoneal, intramuscular, intra-articular, intra-synovial, intrasternal, intrathecal, intrahepatic, intralesional and intracranial injection or infusion techniques. In some embodiments, the compositions are administered orally, intravenously or subcutaneously. In some embodiments, the compositions are administered orally. In some embodiments, the compositions are administered intravenously. In some embodiments, the intravenous administration can be intravenous infusion or intravenous injection. In some embodiments, the compositions are administered by an intravenous infusion. In some embodiments, the compositions are administered by an intravenous injection. In some embodiments, the compositions are administered by subcutaneous injection. In some embodiments, the compositions are administered by intravenous infusion and then subsequently administered by subcutaneous injection. In another embodiment, the checkpoint inhibitor is coadministered with human hyaluronidase subcutaneously. These formulations may be designed to be short-acting, fast-releasing, or long-acting. Furthermore, the compositions may be administered in a local rather than systemic means, such as administration (e.g., by injection) at a tumor site.

Pharmaceutical formulations may be prepared as liquid suspensions or solutions using a liquid, such as an oil, water, an alcohol, and combinations of these. Solubilizing agents such as cyclodextrins may be included. Pharmaceutically suitable surfactants, suspending agents, or emulsifying agents, may be added for oral or parenteral administration. Suspensions may include oils, such as peanut oil, sesame oil, cottonseed oil, corn oil and olive oil. Suspension preparations may also contain esters of fatty acids such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol; ethers, such as poly(ethyleneglycol); petroleum hydrocarbons such as mineral oil and petrolatum; and water.

Sterile injectable forms of these pharmaceutical compositions may be aqueous or oleaginous suspensions. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as sorbitan alkyl esters, such as Tweens or Spans, and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

These pharmaceutical compositions may be orally administered in any orally acceptable dosage form including capsules, tablets, aqueous suspensions or solutions. When aqueous suspensions are required for oral use, the active ingredient is combined with emulsifying and suspending agents. If desired, certain sweetening, flavoring or coloring agents may also be added. For oral administration in a capsule form, useful diluents include lactose and dried cornstarch. In the case of tablets for oral use, carriers that are commonly used include lactose and corn starch. Lubricating agents, such as magnesium stearate, are also typically added. Coatings may be used for a variety of purposes, e.g., to mask taste, to affect the site of dissolution or absorption, or to prolong drug action. Coatings may be applied to a tablet or to granulated particles for use in a capsule.

Alternatively, these pharmaceutical compositions may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

These pharmaceutical compositions may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of the present disclosure include mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active component(s) suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In one embodiment, Compound No. 14 is formulated as a solution for intravenous infusion. In some embodiments, Compound No. 14 is formulated in a solution containing 3 mg/3 mL Compound No. 14 as free base. In one embodiment, the solution of Compound No. 14 can be diluted prior to infusion.

Kits

In some embodiments, the STING agonist or the checkpoint inhibitor described herein may be manufactured for inclusion in a kit. A "kit" is any article of manufacture (e.g., a package or container) comprising at least one reagent or chemotherapeutic agent. A kit for use in the methods herein may comprise a STING agonist, such as Compound No. 14 or a pharmaceutically acceptable salt thereof. In some embodiments, the kit may further include a checkpoint inhibitor, and optionally one or more additional therapeutic agents. In some embodiments, the kit may include Compound No. 14 or a pharmaceutically acceptable salt thereof, a checkpoint inhibitor, and optionally one or more additional therapeutic agents. In some embodiments, the kit may include one or more STING agonists or pharmaceutically acceptable salts thereof. In some embodiments, the kit may include one or more checkpoint inhibitors.

In some embodiments, the present disclosure relates to a kit comprising a medicament for use in treating cancer in a patient in need of such treatment. The kit comprises a medicament comprising a STING agonist, and instructions for administering the STING agonist and a checkpoint inhibitor; or the kit comprises a medicament comprising a checkpoint inhibitor, and instructions for administering the checkpoint inhibitor and a STING agonist. The kit may contain a medicament comprising a STING agonist and a checkpoint inhibitor, and instructions for administering the STING agonist and the checkpoint inhibitor, wherein the medicament is in single dosage form or in separate dosage forms. In some embodiments, the kit optionally comprises one or more additional therapeutic agents.

In some embodiments, a kit comprising a STING agonist and a checkpoint inhibitor may further include another component or reagent. In some embodiments, a reagent in the kit may be a diluent for preparing the STING agonist for administration. In some embodiments, a reagent in the kit may be a diluent for preparing the checkpoint inhibitor for administration. In some embodiments, a component in the kit may be a vessel for mixing the combination of the STING agonist and the checkpoint inhibitor.

In another aspect, the present disclosure relates to a kit for treating cancer comprising at least one medicament comprising at least one dose of Compound No. 14 or a pharmaceutically acceptable salt thereof, and at least one medicament comprising at least one dose of a checkpoint inhibitor, said kit for treating cancer further comprising dosing instructions for administering the medicaments for treatment of the patient in recognized need thereof.

In order that this present disclosure be more fully understood, the following examples are set forth. These examples are illustrative only and are not intended to limit the scope of the present disclosure in any way.

EXAMPLES

Abbreviations

H hour
Min minutes
HPLC High-pressure liquid chromatography
UPLC Ultra-pressure liquid chromatography
NMR Nuclear Magnetic Resonance
THF tetrahydrofuran
WFI Water for Injection
TGI tumor growth inhibition
Mg milligram
$mm^3$ cubic millimeter
HPbCD 2-hydroxypropyl-β-cyclodextrin
CMC carboxymethylcellulose
PO oral
SC subcutaneously
SD starting day
SA single agent
Q3W once every 3 weeks
BLRM Bayesian Logistic Regression Modeling
MTD maximum tolerated dose
PAD pharmacologically active dose
IV intravenous
DLT Dose limiting toxicity
PK Pharmacokinetic
TEAEs Treatment-emergent adverse events
DL Dose level
RP2D recommended phase 2 dose
MABEL minimum anticipated biological effect level Example 1: In Vivo Tumor Efficacy General Analytical Methods Unless otherwise stated $^1$H NMR spectra were obtained using a Varian 300 MHz. Unless otherwise stated HPLC were obtained on Agilent 1100 Series and UPLC were obtained by Water Acuity Systems.

Compound No. 14, as used in the Examples below, can be synthesized according to the procedures recited in Example 14 in PCT publication number WO 2018/100558.

General Experimental Conditions for Anti-Tumor Efficacy in Mouse Tumor Models

Mouse Syngeneic Tumor Models

The following syngeneic models were utilized in each of Studies 1-5, as specified below.

A20 Study 1: A20 is a mouse B-cell lymphoma cell line. A20 mouse syngeneic tumor model was generated by subcutaneous inoculation with $0.4 \times 10^6$ A20 cells (cell suspension) in approximately 9 weeks old female BALB/c mice (Vital River Laboratory Animal Technology Co., Ltd., Beijing, China) in the flank. When the mean tumor volume reached approximately 55 $mm^3$, the animals were randomized into one vehicle control and three treatment groups (n=10/group). Mice were then dosed with PBS or Compound No. 14 or anti-mouse PD-1 antibody or Compound No. 14 plus anti-mouse PD-1 antibody over a 31-day period. Tumor growth and body weight were measured twice per week during the treatment and post-treatment periods, and mice were humanely euthanized once they had reached their humane endpoint.

L5178-R Study 2: L5178-R is a mouse lymphoma cell line. L5178-R mouse syngeneic tumor model was generated by subcutaneous inoculation with 0.2×10⁶ L5178-R cells (cell suspension) in approximately 12 weeks old female DBA/2 mice (Vital River Laboratory Animal Technology Co., Ltd., Beijing, China) in the flank. When the mean tumor volume reached approximately 65 mm³, the animals were randomized into one vehicle control and four treatment groups (n=10/group). Mice were then dosed with PBS or Compound No. 14 or anti-mouse PD-1 antibody or Compound No. 14 plus anti-mouse PD-1 antibody at 10 mg/kg (Q3D×3 & QW×3) over a 10-day period. Tumor growth and body weight were measured twice per week during the treatment and post-treatment periods, and mice were humanely euthanized once they had reached their humane endpoint.

WEHI-3 Study 3: WEHI-3 is a mouse myelomonocytic leukemia cell line. WEHI-3 mouse syngeneic tumor model was generated by subcutaneous inoculation with 0.1×10⁶ WEHI-3 cells (cell suspension) in approximately 11 weeks old female BALB/c mice (Vital River Laboratory Animal Technology Co., Ltd., Beijing, China) in the flank. When the mean tumor volume reached approximately 60 mm³, the animals were randomized into one vehicle control and four treatment groups (n=10/group). Mice were then dosed with PBS or Compound No. 14 or anti-mouse PD-1 antibody or Compound No. 14 plus anti-mouse PD-1 antibody over a 21-day period. Tumor growth and body weight were measured twice per week during the treatment and post-treatment periods, and mice were humanely euthanized once they had reached their humane endpoint.

RM-1 Study 4: RM-1 is a mouse prostate carcinoma cell line. RM-1 mouse syngeneic tumor model was generated by subcutaneous inoculation with 0.8×10⁶ RM-1 cells (cell suspension) in 10 weeks old female C57BL/6 mice (Vital River Laboratory Animal Technology Co., Ltd., Beijing, China) in the flank. When the mean tumor volume reached approximately 60 mm³, the animals were randomized into one vehicle control and four treatment groups (n=10/group). Mice were then dosed with PBS or Compound No. 14 or anti-mouse PD-1 antibody or Compound No. 14 plus anti-mouse PD-1 antibody over a 19-day period. Tumor growth and body weight were measured twice per week during the treatment and post-treatment periods, and mice were humanely euthanized once they had reached their humane endpoint.

L1210 Study 5: L1210 is a mouse leukemia cell line. L1210 mouse syngeneic tumor model was generated by subcutaneous inoculation with 0.02×10⁶ L1210 cells (cell suspension) in approximately 11 weeks old female DBA/2 mice (Vital River Laboratory Animal Technology Co., Ltd., Beijing, China) in the flank. When the mean tumor volume reached approximately 50 mm³, the animals were randomized into one vehicle control and four treatment groups (n=10/group). Mice were then dosed with PBS or Compound No. 14 or anti-mouse PD-1 antibody or Compound No. 14 plus anti-mouse PD-1 antibody over a 15-day period. Tumor growth and body weight were measured twice per week during the treatment and post-treatment periods, and mice were humanely euthanized once they had reached their humane endpoint.

Test Agents

The following test agents were utilized in each of Studies 1-5, as specified below.

A20 Study 1: A 0.025 mg/mL stock solution of Compound No. 14 was formulated in Phosphate-buffered saline (PBS) and administered intravenously (IV) based on exact animal body weight on each day of treatment, using a dosing volume of 10 mL/kg body weight. Final doses received were 0.25 mg/kg. Dosing volume for Compound No. 14 was 0.2 mL. Anti-mouse PD1 antibody (anti-mPD-1) (Bio X Cell, 10 Technology Drive, Suite 2B, West Lebanon, NH 03784) was formulated prior to each injection at 2 mg/mL in Phosphate-buffered saline (PBS) and administered intraperitoneally (IP) based on exact body weight on each day of treatment, using a dosing volume of 5 mL/kg resulting in a 10 mg/kg dose. Dosing volume for anti-mPD-1 was 0.1 mL. Compound No. 14 was administered on a Q3D schedule for 3 cycles till Day 6 (Day 0, 3 and 6) in single agent treatment group and in combination treatment group, and anti-mPD-1 administered on a Q3D schedule for 3 cycles till Day 6 and a QW schedule for 3 weeks till Day 27 (Day 0, 3, 6, 13, 20, and 27) in single agent treatment group and in combination treatment group.

L5178-R Study 2: A 0.025 mg/mL stock solution of Compound No. 14 was formulated in Phosphate-buffered saline (PBS) and administered intravenously (IV) based on exact animal body weight on each day of treatment, using a dosing volume of 10 mL/kg body weight. Final doses received were 0.25 mg/kg. Dosing volume for Compound No. 14 was 0.2 mL. Anti-mouse PD1 antibody (anti-mPD-1) (Bio X Cell, 10 Technology Drive, Suite 2B, West Lebanon, NH 03784) was formulated prior to each injection at 2 mg/mL in Phosphate-buffered saline (PBS) and administered intraperitoneally (IP) based on exact body weight on each day of treatment, using a dosing volume of 5 mL/kg resulting in a 10 mg/kg dose. Dosing volume for anti-mPD-1 was 0.1 mL. Compound No. 14 was administered on a Q3D schedule for 3 cycles till Day 6 (Day 0, 3 and 6) in single agent treatment group and in combination treatment group, and anti-mPD-1 administered on a Q3D schedule for 3 cycles till Day 6 (Day 0, 3 and 6) in single agent treatment group and in combination treatment group.

WEHI-3 Study 3: A 0.025 mg/mL stock solution of Compound No. 14 was formulated in Phosphate-buffered saline (PBS) and administered intravenously (IV) based on exact animal body weight on each day of treatment, using a dosing volume of 10 mL/kg body weight. Final doses received were 0.25 mg/kg. Dosing volume for Compound No. 14 was 0.2 mL. Anti-mouse PD1 antibody (anti-mPD-1) (Bio X Cell, 10 Technology Drive, Suite 2B, West Lebanon, NH 03784) was formulated prior to each injection at 2 mg/mL in Phosphate-buffered saline (PBS) and administered intraperitoneally (IP) based on exact body weight on each day of treatment, using a dosing volume of 5 mL/kg resulting in a 10 mg/kg dose. Dosing volume for anti-mPD-1 was 0.1 mL. Compound No. 14 was administered on a Q3D schedule for 3 cycles till Day 6 (Day 0, 3 and 6) in single agent treatment group and in combination treatment group, and anti-mPD-1 administered on a Q3D schedule for 3 cycles till Day 6 and a QW schedule for 1 week till Day 13 (Day 0, 3, 6 and 13) in single agent treatment group and in combination treatment group.

RM-1 Study 4: A 0.025 mg/mL stock solution of Compound No. 14 was formulated in Phosphate-buffered saline (PBS) and administered intravenously (IV) based on exact animal body weight on each day of treatment, using a dosing volume of 10 mL/kg body weight. Final doses received were 0.25 mg/kg. Dosing volume for Compound No. 14 was 0.2 mL. Anti-mouse PD1 antibody (anti-mPD-1) (Bio X Cell, 10 Technology Drive, Suite 2B, West Lebanon, NH 03784) was formulated prior to each injection at 2 mg/mL in Phosphate-buffered saline (PBS) and administered intraperitoneally (IP) based on exact body weight on each day of treatment, using a dosing volume of 5 mL/kg resulting in a 10 mg/kg dose. Dosing volume for anti-mPD-1 was 0.1 mL. Compound No. 14 was administered on a Q3D schedule for 3 cycles till Day 6 (Day 0, 3 and 6) in single agent treatment group and in combination treatment group, and anti-mPD-1 administered on a Q3D schedule for 3 cycles till Day 6 and a QW schedule for 1 week till Day 13 (Day 0, 3, 6 and 13) in single agent treatment group and in combination treatment group.

L1210 Study 5: A 0.025 mg/mL stock solution of Compound No. 14 was formulated in Phosphate-buffered saline (PBS) and administered intravenously (IV) based on exact animal body weight on each day of treatment, using a dosing volume of 10 mL/kg body weight. Final doses received were 0.25 mg/kg. Dosing volume for Compound No. 14 was 0.2 mL. Anti-mouse PD1 antibody (anti-mPD-1) (Bio X Cell, 10 Technology Drive, Suite 2B, West Lebanon, NH 03784) was formulated prior to each injection at 2 mg/mL in Phosphate-buffered saline (PBS) and administered intraperitoneally (IP) based on exact body weight on each day of treatment, using a dosing volume of 5 mL/kg resulting in a 10 mg/kg dose. Dosing volume for anti-mPD-1 was 0.1 mL. Compound No. 14 was administered on a Q3D schedule for 3 cycles till Day 6 (Day 0, 3 and 6) in single agent treatment group and in combination treatment group, and anti-mPD-1 administered on a Q3D schedule for 3 cycles till Day 6 and a QW schedule for 1 week till Day 13 (Day 0, 3, 6 and 13) in single agent treatment group and in combination treatment group.

Tumor Measurements:

Tumors were measured twice weekly using vernier calipers. Tumor volumes were calculated using standard equation: $V=W^2 \times L/2$, where V=volume, W=width, and L=length for the tumor. When mean tumor volumes reached approximately 55 mm$^3$ for study 1, 65 mm$^3$ for study 2, 60 mm$^3$ for study 3, 60 mm$^3$ for study 4, 50 mm$^3$ for study 5. Mice were randomized into groups of 4 (n=10/group) in Study 1-5, and dosed with vehicle (PBS), Compound No. 14, anti-mPD-1, or the combination of Compound No. 14 plus anti-mPD-1 at various doses and schedules. Tumor size and body weight were measured twice a week for the duration of the study. Mice were euthanized when their tumor volumes reaches greater than 10% of animal's body weight or when an individual tumor exceeded the humane end-point for size (the length of tumor exceeded 2 cm).

Statistical Analysis of Comparing Different Treatments in Mouse Syngeneic Tumor Models The following statistical analysis methods were utilized in studies 1-5.

All tumor volumes had a value of 5 added to them before log transformation. After the transformation, linear interpolation was used to estimate the time (in days) since randomization each mouse's tumor volume reaches 1000 mm$^3$. We consider the event of a mouse's tumor reaching 1000 mm$^3$ as "tumor progression" event and call the aforementioned estimated time as time-to-progression (TTP). In case of a mouse's tumor having not reached 1000 mm$^3$ at the end of study, the last day the mouse was on study was recorded and right-censored. For each pair of treatments of interest, a parametric survival model that assumes a Weibull distribution on TTP was used to estimate the hazard ratio (HR) between two treatment arms. HR reflects the ratio of the hazards the mice of the two treatment arms experience progression events at any timepoint throughout the study. A HR between treatment A and B that is smaller than 1 suggests better efficacy for treatment A than B. Standard errors (SE) and 95% confidence intervals (CI) were also calculated to describe the uncertainties of the estimated HRs. Finally, two types of tests were used to calculate the P-values in order to assess the statistical significance of the difference between the two treatments: 1) A Wald test p-value from the Weibull survival model; 2) a non-parametric log-rank test.

Results

A20 Study 1: The combination arms of Compound No. 14 with anti-mouse PD-1 antibody yielded combination benefit during the 31-day treatment phase of the A20 study when compared to either the Compound No. 14 or anti-mouse PD-1 antibody only arms. The anti-mouse PD-1 antibody only arm achieved one complete response maintained throughout the 31 days, and the Compound No. 14 arm also achieved one complete response. In contrast, the combination arm of Compound No. 14 with anti-mouse PD-1 antibody saw four complete responses. Weibull regression hazard ratios were significant relative to both control arms, although the Compound No. 14 with anti-mouse PD-1 antibody versus the Compound No. 14 alone was not quite significant (p=0.067) when evaluated by the log-rank test.

The treatment groups from Study 1 are shown in Table 1a. The combination effect for the treatment period is shown in Table 1a as well. Progression-free survival Kaplan-Meier curves are shown during the treatment period in FIG. 1a. Tumor growth curves are shown during the treatment period in FIG. 1b.

L5178-R Study 2: The combination arms of Compound No. 14 with anti-mouse PD-1 antibody yielded combination benefit during the 6-day treatment phase of the L5178-R study when compared to anti-mouse PD-1 antibody only arm, but not the Compound No. 14 arm. No complete responses were seen in this study. Weibull regression hazard ratios were significant relative to the anti-mouse PD-1 antibody control arm.

The treatment groups from Study 2 are shown in Table 1a. The combination effect for the treatment period is shown in Table 1a as well. Progression-free survival Kaplan-Meier curves are shown during the treatment period in FIG. 2a. Tumor growth curves are shown during the treatment period in FIG. 2b.

WEHI-3 Study 3: The combination arms of Compound No. 14 with anti-mouse PD-1 antibody yielded combination benefit during the 14-day treatment phase of the WEHI-3 study when compared to anti-mouse PD-1 antibody only arm, but not the Compound No. 14 arm. No complete responses were seen in this study. Weibull regression hazard ratios were significant relative to the anti-mouse PD-1 antibody control arm.

The treatment groups from Study 3 are shown in Table 1a. The combination effect for the treatment period is shown in Table 1a as well. Progression-free survival Kaplan-Meier curves are shown during the treatment period in FIG. 3a. Tumor growth curves are shown during the treatment period in FIG. 3b.

RM-1 Study 4: The combination arms of Compound No. 14 with anti-mouse PD-1 antibody yielded combination benefit during the 14-day treatment phase of the RM-1 study when compared to anti-mouse PD-1 antibody only arm, but not the Compound No. 14 arm. No complete responses were seen in this study. Weibull regression hazard ratios were significant relative to the anti-mouse PD-1 antibody control arm.

The treatment groups from Study 4 are shown in Table 1a. The combination effect for the treatment period is shown in Table 1a as well. Progression-free survival Kaplan-Meier curves are shown during the treatment period in FIG. 4a. Tumor growth curves are shown during the treatment period in FIG. 4b.

L1210 Study 5: The combination arms of Compound No. 14 with anti-mouse PD-1 antibody yielded combination benefit during the 11-day treatment phase of the L1210 study when compared to either the Compound No. 14 or anti-mouse PD-1 antibody only arms. No complete responses were seen in this study. Weibull regression hazard ratios were significant relative to both control arms.

The treatment groups from Study 5 are shown in Table 1a. The combination effect for the treatment period is shown in Table 1a as well. Progression-free survival Kaplan-Meier curves are shown during the treatment period in FIG. 5a. Tumor growth curves are shown during the treatment period in FIG. 5b.

TABLE 1a

| Model | Comparison | HR (Weibull) | 95% CI (Weibull) | SE (Weibull) | P-value (Weibull) | P-value (log-rank) |
|---|---|---|---|---|---|---|
| A20 | Anti-PD1 vs PBS | 0.375 | (0.135, 1.04) | 0.196 | 0.0355 | 0.204 |
| A20 | Compound No. 14 vs PBS | 0.104 | (0.0291, 0.374) | 0.0679 | 1.91e−06 | 0.00188* |
| A20 | Compound No. 14 + Anti-PD1 vs Anti-PD1 | 0.122 | (0.0311, 0.478) | 0.0849 | 0.00381 | 0.0133* |
| A20 | Compound No. 14 + Anti-PD1 vs Compound No. 14 | 0.233 | (0.0605, 0.894) | 0.16 | 0.0449 | 0.0674 |
| L5178 | Anti-PD1 vs PBS | 2.15 | (0.815, 5.67) | 1.06 | 0.092 | 0.264 |
| L5178 | Compound No. 14 vs PBS | 0.544 | (0.224, 1.32) | 0.246 | 0.174 | 0.167 |
| L5178 | Compound No. 14 + Anti-PD1 vs Anti-PD1 | 0.0581 | (0.0142, 0.238) | 0.0418 | 2.37e−10 | 2.8e−05* |
| L5178 | Compound No. 14 + Anti-PD1 vs Compound No. 14 | 0.484 | (0.197, 1.19) | 0.222 | 0.105 | 0.13 |
| RM-1 | Anti-PD1 vs PBS | 1.45 | (0.583, 3.6) | 0.673 | 0.421 | 0.534 |
| RM-1 | Compound No. 14 vs PBS | 0.425 | (0.175, 1.03) | 0.192 | 0.059 | 0.0379* |
| RM-1 | Compound No. 14 + Anti-PD1 vs Anti-PD1 | 0.315 | (0.126, 0.787) | 0.147 | 0.0146 | 0.0254* |
| RM-1 | Compound No. 14 + Anti-PD1 vs Compound No. 14 | 1.73 | (0.689, 4.33) | 0.811 | 0.224 | 0.316 |
| WEHI3 | Anti-PD1 vs PBS | 0.278 | (0.092, 0.841) | 0.157 | 0.00632 | 0.0986 |
| WEHI3 | Compound No. 14 vs PBS | 0.0487 | (0.0108, 0.219) | 0.0374 | 2.44e−10 | 4.35e−06* |
| WEHI3 | Compound No. 14 + Anti-PD1 vs Anti-PD1 | 0.253 | (0.0999, 0.642) | 0.12 | 0.00264 | 0.00123* |
| WEHI3 | Compound No. 14 + Anti-PD1 vs Compound No. 14 | 2.14 | (0.783, 5.85) | 1.1 | 0.102 | 0.869 |
| L1210 | Anti-PD1 vs PBS | 0.0233 | (0.00531, 0.103) | 0.0176 | 7.84e−17 | 2.97e−06* |
| L1210 | Compound No. 14 vs PBS | 0.118 | (0.039, 0.357) | 0.0667 | 1.84e−06 | 0.000113* |
| L1210 | Compound No. 14 + Anti-PD1 vs Anti-PD1 | 0.281 | (0.109, 0.723) | 0.136 | 0.00472 | 0.00286* |
| L1210 | Compound No. 14 + Anti-PD1 vs Compound No. 14 | 0.0515 | (0.0155, 0.172) | 0.0317 | 7.29e−11 | 6.63e−06* |

*Statistically significant Hazards Ratio based upon log-rank test.

Additional Mouse Syngeneic Studies

Unlike in the A20, L5178-R, WEHI-3, RM-1 and L1210 syngeneic models, no combination benefit of Compound No. 14 plus anti-mouse PD-1 antibody was observed in the mouse breast carcinoma 4T1, mouse melanoma B16F10, mouse leukemia C1498, mouse colon adenocarcinoma Colon26, mouse colon adenocarcinoma CT26, mouse lymphoma E.G7-OVA, mouse lymphoma EL4, mouse breast carcinoma EMT6, mouse hepatoma H22, mouse plasmacytoma J558, mouse breast adenocarcinoma JC, mouse lung carcinoma KLN205, mouse Lewis lung carcinoma LLC1, mouse Lewis lung carcinoma LLC-1 luc, mouse colon adenocarcinoma MC38, mouse lymphoma P388D1, mouse pancreatic ductal adenocarcinoma PANCO2 and mouse kidney carcinoma RENCA models, under similar experimental conditions and procedures in Studies 1-5.

Example 2: Clinical Study Evaluating Compound No. 14 in Combination with an Anti-PD-1 Antibody in Treatment of Patients with Metastatic Solid Tumors A phase 1, open-label, parallel assignment, dose escalation study will be conducted to evaluate safety, tolerability, pharmacokinetics (PK), and pharmacodynamics of Compound No. 14 as a single agent (SA) and in combination with pembrolizumab in adult patients with metastatic solid tumors. This information will be used to independently evaluate both the pharmacologically active dose (PAD) and maximum tolerated dose (MTD) to establish the recommended phase 2 dose (RP2D) for the SA and combination with pembrolizumab. Dose escalation may stop after determination of a PAD but before determination of an MTD, based on discussion of safety data by the investigators and the sponsor.

Approximately 100 patients will be enrolled in this study. Once enrolled, patients will be administered Compound No. 14 intravenously (IV) on Days 1, 4, 8, and 11 of every 21-day dosing cycle in both the Compound No. 14 SA and combination with pembrolizumab arms. All patients will be hospitalized for treatment and monitoring through at least Cycle 1 Day 9. Patients can be discharged 24 hours after Day 8 infusion if there are no clinical concerns (i.e., fever, hypotension, or other clinical safety issues). If clinical safety, PK, and pharmacodynamics are supportive, the dosing schedule may be modified to evaluate a less intensive administration of Compound No. 14 on Days 1 and 8 in cycles of 21 days without requiring a protocol amendment. Alternate dosing schedules may also be considered, if the collective data on safety, PK, and pharmacodynamics support it. Also, patients with clinical benefit can be changed to this less-frequent schedule after Cycle 6 if the investigator, in agreement with the patient, considers that continuing with the intensive schedule would negatively impact the patient's well-being.

Single Agent Compound No. 14 Arm

The proposed initial explorable dose range is 0.2 to 3.5 mg (with a provision for dose level [DL]-1 of 0.1 mg if the starting dose of 0.2 mg is not tolerated). The starting dose is calculated using a combined minimum anticipated biological effect level (MABEL) and nonclinical toxicology approach. Doses of greater than 3.5 mg may be explored if the last DL is considered safe and tolerable. The upper DL of 3.5 mg corresponds approximately to the human equivalent dose that is slightly above the MTD in monkeys. For the first 3 patients at a given DL, patient enrollment will be staggered with a planned 4-day hold between each patient. If more than 3 patients are to be enrolled in a DL, or if de-escalation is indicated, this hold may not be required if there are no clinically significant safety findings suggestive of infusion reaction or cytokine release syndrome. During the study, this 4-day hold may be reconsidered in discussions with study investigators and sponsors.

Compound No. 14 in Combination with Pembrolizumab Arm

A second arm will evaluate the safety, tolerability, PK, and pharmacodynamics of Compound No. 14 in combination with the approved dose and schedule of pembrolizumab (200 mg, once every 3 weeks [Q3W]). This second arm will only be initiated when at least 2 DLs of SA Compound No. 14 have been evaluated and deemed safe and tolerated. If there is no need for a dose reduction to DL-1 in the SA arm, the starting dose of Compound No. 14 in this arm will be 0.2 mg (Compound No. 14 MABEL) administered on a Day 1, 4, 8, and 11 dosing schedule in combination with 200 mg pembrolizumab administered once every 3 weeks. For Cycle 1 only, Compound No. 14 will be administered on Day 1 and pembrolizumab will be administered on Day 2 for a better assessment of safety. For the rest of the administrations starting on Cycle 2 Day 1, both drugs will be administered on Day 1, starting with Compound No. 14 followed by pembrolizumab with a 1-hour interval between the 2 drugs. Less frequent administration of Compound No. 14 in combination with pembrolizumab, such as Day 1 and Day 8 administration in 21-day cycles, may be considered if clinical safety and/or PK/pharmacodynamics data support it. Alternate dosing schedules may also be considered, if the collective data on safety, PK, and pharmacodynamics support it.

The study design is composed of a dose escalation part followed by dose expansion cohorts for both Compound No. 14 SA and combination arms. Dose escalation of Compound No. 14 as a SA and in combination with pembrolizumab will follow an adaptive design using Bayesian Logistic Regression Modeling (BLRM). BLRM with overdose control will be used to inform dose escalation decisions and MTD estimation for the SA and combination arms, however a combination of PK and pharmacodynamic data will be used for estimation of PAD. Once a PAD for Compound No. 14 as a SA or in combination with pembrolizumab has been determined, either Compound No. 14 SA or combination expansion cohorts may be initiated without the identification of a SA or combination MTD, respectively. For both the SA and combination arms, 3 patients will be initially enrolled at the starting DL followed by 3+3+3 dose escalation rules. Starting from the second DL of patients, the BLRM with overdose control will be used for all subsequent dose recommendations, along with consideration of other non-dose-limiting toxicity (DLT) safety and available PK data, for both the SA and combination arms. The final decision on next DL will be made jointly by the sponsor and the participating investigators, considering BLRM output and any other available clinical or translational information, and within the boundaries of the DLs.

Once the MTD and/or PAD are determined for Compound No. 14 as a SA or in combination with pembrolizumab, expansion cohorts of approximately 15 patients treated with Compound No. 14 SA or Compound No. 14 in combination with pembrolizumab may be initiated to better evaluate safety and tolerability at that dose. The expansion cohorts may be initiated once the PAD has been identified and need not wait for determination of MTD. The ability to expand to more than 1 dose if the MTD or PAD is not elucidated from the dose escalation phase may be agreed upon between the sponsor and investigators. In principle, these cohorts will enroll the same patient population as in the dose escalation phase; however, some enrichment strategy can be put in place for these expansion cohorts if supported either by literature/publication, nonclinical/translational work or evidence of antitumor activity during escalation phases. No formal sample size calculation is performed for the expansion cohorts.

Toxicity will be evaluated according to the National Cancer Institute Common Terminology Criteria for Adverse Events, Version 5.0. A DLT will be defined as any of the treatment-emergent adverse events (TEAEs) described in detail, but not limited to, those that occur during Cycle 1 and are considered by the investigator to be at least possibly related to Compound No. 14 as a SA or in combination with pembrolizumab. TEAEs meeting DLT definitions occurring in later cycles will be considered in the determination of PAD and RP2D of Compound No. 14 that might be equal to or lower than the MTD, both as a SA and in combination with pembrolizumab.

Patients who have tolerated treatment with Compound No. 14 well at the initially assigned dose (i.e., have at least completed Cycle 1 without DLT) and are benefitting from study treatment based on investigator assessment may be allowed to increase their dose of Compound No. 14 in subsequent cycles of treatment upon discussion with the sponsor. This may be considered only if all patients in the next DL cohort have not experienced a DLT-like toxicity or discontinued due to an adverse event after 3 cycles of treatment and a decision has been made that this DL does not exceed the MTD. If any patient in the next DL cohort progresses during the first 3 cycles of treatment, this will not prohibit intrapatient dose escalation from the previous dose.

During dose escalation, patients not receiving the scheduled doses in Cycle 1 for reasons other than DLT will be replaced.

This study will enroll up to approximately 100 subjects.

Primary Endpoints

The primary endpoints for this phase 1 trial may include Frequency and severity of TEAEs; Number of patients with DLTs; Number/percentage of patients with 1 or more serious adverse event; and Number/percentage of patients with 1 or more TEAE leading to dose modifications and treatment discontinuations.

The trial will be conducted in conformance with Good Clinical Practices.

Example 3: Clinical Study Evaluating Compound No. 14 in Combination with an Anti-PD-1 Antibody in Treatment of Patients with Metastatic Solid Tumors A phase 1, open-label, parallel assignment, dose escalation study will be conducted to evaluate safety, tolerability, pharmacokinetics (PK), and pharmacodynamics of Compound No. 14 as a single agent (SA) and in combination with pembrolizumab in adult patients with metastatic solid tumors. This information will be used to independently evaluate both the pharmacologically active dose (PAD) and maximum tolerated dose (MTD) to establish the recommended phase 2 dose (RP2D) for the SA and combination with pembrolizumab. Dose escalation may stop after determination of a PAD but before determination of an MTD, based on discussion of safety data by the investigators and the sponsor.

Approximately 100 patients will be enrolled in this study. Once enrolled, patients will be administered Compound No. 14 as an intravenous (IV) infusion on Days 1, 8, and 15 of every 21-day dosing cycle in both the Compound No. 14 SA and combination with pembrolizumab arms. All patients will be hospitalized for treatment and monitoring through at least Cycle 1 Day 9. Patients can be discharged 24 hours after Day 8 infusion if there are no clinical concerns (i.e., fever, hypotension, or other clinical safety issues). If clinical safety, PK, and pharmacodynamics are supportive, the dosing schedule may be modified to evaluate a less intensive administration of Compound No. 14 on Days 1 and 8 in cycles of 21 days without requiring a protocol amendment. Alternate dosing schedules may also be considered, if the collective data on safety, PK, and pharmacodynamics support it. Also, patients with clinical benefit can be changed to this less-frequent schedule after Cycle 6 if the investigator, in agreement with the patient, considers that continuing with the intensive schedule would negatively impact the patient's well-being.

Single Agent Compound No. 14 Arm

The proposed initial explorable dose range is 0.2 to 3.5 mg (with a provision for dose level [DL]-1 of 0.1 mg if the starting dose of 0.2 mg is not tolerated). The starting dose is calculated using a combined minimum anticipated biological effect level (MABEL) and nonclinical toxicology approach. Doses of greater than 3.5 mg may be explored if the last DL is considered safe and tolerable. The upper DL of 3.5 mg corresponds approximately to the human equivalent dose that is slightly above the MTD in monkeys. For the first 3 patients at a given DL, patient enrollment will be staggered with a planned 4-day hold between each patient. If more than 3 patients are to be enrolled in a DL, or if de-escalation is indicated, this hold may not be required if there are no clinically significant safety findings suggestive of infusion reaction or cytokine release syndrome. During the study, this 4-day hold may be reconsidered in discussions with study investigators and sponsors.

Compound No. 14 in Combination with Pembrolizumab Arm

A second arm will evaluate the safety, tolerability, PK, and pharmacodynamics of Compound No. 14 in combination with the approved dose and schedule of pembrolizumab (200 mg, once every 3 weeks [Q3W]). This second arm will only be initiated when at least 2 DLs of SA Compound No. 14 have been evaluated and deemed safe and tolerated. If there is no need for a dose reduction to DL-1 in the SA arm, the starting dose of Compound No. 14 in this arm will be 0.2 mg (Compound No. 14 MABEL) administered on a Day 1, 8, and 15 dosing schedule in combination with 200 mg pembrolizumab administered on Day 1 of the 21 day dosing cycle. For Cycle 1 only, Compound No. 14 can be administered on Day 1 and pembrolizumab can be administered on Day 2 for a better assessment of safety. For the rest of the administrations starting on Cycle 2 Day 1, both drugs will be administered on Day 1, starting with Compound No. 14 followed by pembrolizumab with a 1-hour interval between the 2 drugs. Less frequent administration of Compound No. 14 in combination with pembrolizumab, such as Day 1 and Day 8 administration in 21-day cycles, may be considered if clinical safety and/or PK/pharmacodynamics data support it. Alternate dosing schedules may also be considered, if the collective data on safety, PK, and pharmacodynamics support it.

The study design is composed of a dose escalation part followed by dose expansion cohorts for both Compound No. 14 SA and combination arms. Dose escalation of Compound No. 14 as a SA and in combination with pembrolizumab will follow an adaptive design using Bayesian Logistic Regression Modeling (BLRM). BLRM with overdose control will be used to inform dose escalation decisions and MTD estimation for the SA and combination arms, however a combination of PK and pharmacodynamic data will be used for estimation of PAD. Once a PAD for Compound No. 14 as a SA or in combination with pembrolizumab has been determined, either Compound No. 14 SA or combination expansion cohorts may be initiated without the identification of a SA or combination MTD, respectively. For both the SA and combination arms, 3 patients will be initially enrolled at the starting DL followed by 3+3+3 dose escalation rules. Starting from the second DL of patients, the BLRM with overdose control will be used for all subsequent dose recommendations, along with consideration of other non-dose-limiting toxicity (DLT) safety and available PK data, for both the SA and combination arms. The final decision on next DL will be made jointly by the sponsor and the participating investigators, considering BLRM output and any other available clinical or translational information, and within the boundaries of the DLs.

Once the MTD and/or PAD are determined for Compound No. 14 as a SA or in combination with pembrolizumab, expansion cohorts of approximately 15 patients treated with Compound No. 14 SA or Compound No. 14 in combination with pembrolizumab may be initiated to better evaluate safety and tolerability at that dose. The expansion cohorts may be initiated once the PAD has been identified and need not wait for determination of MTD. The ability to expand to more than 1 dose if the MTD or PAD is not elucidated from the dose escalation phase may be agreed upon between the sponsor and investigators. In principle, these cohorts will enroll the same patient population as in the dose escalation phase; however, some enrichment strategy can be put in place for these expansion cohorts if supported either by literature/publication, nonclinical/translational work or evidence of antitumor activity during escalation phases. No formal sample size calculation is performed for the expansion cohorts.

Toxicity will be evaluated according to the National Cancer Institute Common Terminology Criteria for Adverse Events, Version 5.0. A DLT will be defined as any of the treatment-emergent adverse events (TEAEs) described in detail, but not limited to, those that occur during Cycle 1 and are considered by the investigator to be at least possibly related to Compound No. 14 as a SA or in combination with pembrolizumab. TEAEs meeting DLT definitions occurring in later cycles will be considered in the determination of PAD and RP2D of Compound No. 14 that might be equal to or lower than the MTD, both as a SA and in combination with pembrolizumab.

Patients who have tolerated treatment with Compound No. 14 well at the initially assigned dose (i.e., have at least completed Cycle 1 without DLT) and are benefitting from study treatment based on investigator assessment may be allowed to increase their dose of Compound No. 14 in subsequent cycles of treatment upon discussion with the sponsor. This may be considered only if all patients in the next DL cohort have not experienced a DLT-like toxicity or discontinued due to an adverse event after 3 cycles of treatment and a decision has been made that this DL does not exceed the MTD. If any patient in the next DL cohort progresses during the first 3 cycles of treatment, this will not prohibit intrapatient dose escalation from the previous dose.

During dose escalation, patients not receiving the scheduled doses in Cycle 1 for reasons other than DLT will be replaced.

This study will enroll up to approximately 100 subjects.
Primary Endpoints

The primary endpoints for this phase 1 trial may include Frequency and severity of TEAEs; Number of patients with DLTs; Number/percentage of patients with 1 or more serious adverse event; and Number/percentage of patients with 1 or more TEAE leading to dose modifications and treatment discontinuations.

The trial will be conducted in conformance with Good Clinical Practices.

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

What is claimed is:

1. A method of treating a patient having cancer, comprising:
administering to a patient in need of said treating Compound No. 14, having the following structure:

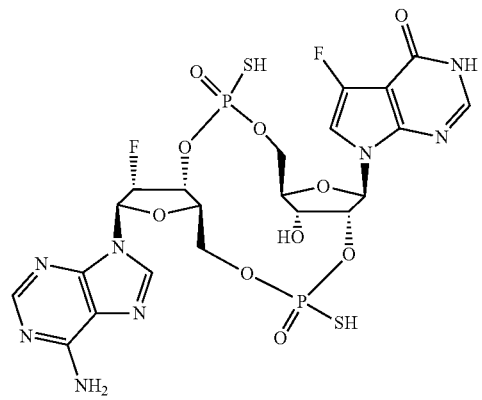 [SMILES: Nc1ncnc2c1ncn2[C@@H]1O[C@@H]2COP(=O)(S)O[C@@H]3[C@H](O)[C@@H](COP(=O)(S)O[C@H]2[C@H]1F)O[C@H]3n1cc(F)c2c(=O)[nH]cnc21]

or a pharmaceutically acceptable salt thereof, and
a checkpoint inhibitor, wherein the checkpoint inhibitor is an anti-PD1 antibody or an anti-PD-L1 antibody, and wherein administering Compound No. 14 and the checkpoint inhibitor provides a synergistic effect.

2. The method of claim 1, wherein the cancer is a PD-1 positive cancer, or a PD-L1 positive cancer.

3. The method of claim 1, wherein the cancer is melanoma, lung cancer, renal cancer, lymphoma, head and neck cancer, urothelial cancer, prostate cancer, bladder cancer, breast cancer, gastric cancer, colorectal cancer, leukemia, cervical cancer, microsatellite instability-high cancer, hepatocellular carcinoma, or Merkel cell carcinoma.

4. The method of claim 3, wherein the cancer is melanoma or lung cancer and wherein the melanoma is metastatic melanoma, unresectable melanoma, or cutaneous melanoma, and the lung cancer is non-small cell lung cancer or small cell lung cancer.

5. The method of claim 4, wherein the cancer is non-small cell lung cancer and wherein the non-small cell lung cancer is metastatic non-small cell lung cancer, metastatic squamous non-small cell lung cancer, or metastatic nonsquamous non-small cell lung cancer.

6. The method of claim 1, wherein the cancer is a metastatic solid tumor.

7. The method of claim 1, wherein the checkpoint inhibitor is an anti-PD-1 antibody selected from the group consisting of nivolumab, pembrolizumab, lambrolizumab, pidilizumab, BMS-936559, and AMP-224.

8. The method of claim 1, wherein the checkpoint inhibitor is an anti-PD-L1 antibody selected from the group consisting of atezolizumab, durvalumab, avelumab, YW243.55.S70, MEDI-4736, MSB-0010718C, LY3300054, BMS-936559, MPDL3280A, and MDX-1105.

9. The method of claim 1, wherein Compound No. 14, or a pharmaceutically acceptable salt thereof, is administered orally, intravenously, or by intravenous infusion.

10. The method of claim 1, wherein the checkpoint inhibitor is administered in an amount of 200 mg.

11. The method of claim 1, wherein Compound No. 14 is administered in an amount of from 0.1 mg to 3.5 mg, or in an amount of from 0.2 mg to 3.5 mg, or in an amount of from 0.1 mg to 1.2 mg, or in an amount of from 0.2 mg to 1.2 mg.

12. The method of claim 1, wherein the checkpoint inhibitor is administered in an amount of 200 mg, and Compound No. 14 is administered in an amount of from 0.1 mg to 3.5 mg, or in an amount of from 0.2 mg to 3.5 mg, or in an amount of from 0.1 mg to 1.2 mg, or in an amount of from 0.2 mg to 1.2 mg.

13. The method of claim 1, where Compound No. 14 and the checkpoint inhibitor are administered concurrently or sequentially in separate pharmaceutical compositions.

14. The method of claim 1, wherein the checkpoint inhibitor is administered once every twelve weeks, once every four weeks, once every three weeks, once every two weeks, once every week, twice a week, three times a week, or daily.

15. The method of claim 14, wherein the checkpoint inhibitor is administered once every three weeks.

16. The method of claim 1, wherein the checkpoint inhibitor is administered on Day 1 or Day 2 of a treatment cycle.

17. The method of claim 16, wherein the treatment cycle is 14 days, 21 days, 28 days, or 84 days.

18. The method of claim 1, wherein Compound No. 14 is administered on Days 1, 4, 8, and 11 of a treatment cycle, on Days 1 and 8 of a treatment cycle, or on Days 1, 8, and 15 of a treatment cycle.

19. The method of claim 1, wherein Compound No. 14 is administered on Days 1, 8, and 15 of a treatment cycle and the checkpoint inhibitor is administered on Day 1 of a treatment cycle.

* * * * *